US010358414B2

(12) United States Patent
Neary et al.

(10) Patent No.: US 10,358,414 B2
(45) Date of Patent: *Jul. 23, 2019

(54) SUBSTITUTED N-ACETYL-L-CYSTEINE DERIVATIVES AND RELATED COMPOUNDS

(71) Applicant: Promentis Pharmaceuticals, Inc., Milwaukee, WI (US)

(72) Inventors: Michael Neary, Cedarburg, WI (US); James Nieman, Sherwood Park (CA); Steven Tanis, Carlsbad, CA (US); Daniel Lawton, Bayside, WI (US); Garry Smith, Royersford, PA (US)

(73) Assignee: Promentis Pharmaceuticals, Inc., Milwaukee, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/481,728

(22) Filed: Apr. 7, 2017

(65) Prior Publication Data

US 2017/0210716 A1    Jul. 27, 2017

Related U.S. Application Data

(63) Continuation of application No. 14/535,855, filed on Nov. 7, 2014, now Pat. No. 9,630,937.

(60) Provisional application No. 61/902,052, filed on Nov. 8, 2013, provisional application No. 61/902,669, filed on Nov. 11, 2013.

(51) Int. Cl.

| | |
|---|---|
| *C07D 277/08* | (2006.01) |
| *C07D 241/08* | (2006.01) |
| *C07C 323/60* | (2006.01) |
| *C07C 327/26* | (2006.01) |
| *C07C 329/06* | (2006.01) |
| *C07C 327/34* | (2006.01) |
| *C07D 327/04* | (2006.01) |
| *C07C 323/57* | (2006.01) |
| *C07C 323/58* | (2006.01) |
| *C07C 323/59* | (2006.01) |
| *C07C 327/32* | (2006.01) |
| *C07D 277/14* | (2006.01) |
| *A61K 31/265* | (2006.01) |
| *A61K 31/165* | (2006.01) |
| *A61K 31/426* | (2006.01) |
| *A61K 31/513* | (2006.01) |

(52) U.S. Cl.
CPC .......... *C07C 327/34* (2013.01); *C07C 323/57* (2013.01); *C07C 323/58* (2013.01); *C07C 323/59* (2013.01); *C07C 323/60* (2013.01); *C07C 327/26* (2013.01); *C07C 327/32* (2013.01); *C07C 329/06* (2013.01); *C07D 241/08* (2013.01); *C07D 277/08* (2013.01); *C07D 277/14* (2013.01); *C07D 327/04* (2013.01); *A61K 31/165* (2013.01); *A61K 31/265* (2013.01); *A61K 31/426* (2013.01); *A61K 31/513* (2013.01)

(58) Field of Classification Search
CPC .......................... C07D 277/08; C07D 241/08; C07C 323/60; C07C 329/06
See application file for complete search history.

(56) References Cited

U.S. PATENT DOCUMENTS

| | | | |
|---|---|---|---|
| 3,431,186 A | 3/1969 | Horner et al. | |
| 5,637,616 A | 6/1997 | Sharpe et al. | |
| 7,829,709 B1 | 11/2010 | Cook et al. | |
| 8,173,809 B2 | 5/2012 | Cook et al. | |
| 8,354,449 B2 | 1/2013 | Goldstein | |
| 8,524,772 B2 | 9/2013 | Arad et al. | |
| 8,624,052 B2 | 1/2014 | Johnson et al. | |
| 8,802,635 B2 | 8/2014 | Mograbi et al. | |
| 8,815,905 B2 | 8/2014 | Wolf et al. | |
| 8,937,099 B2 | 1/2015 | Goldstein | |
| 8,962,692 B2 | 2/2015 | Cook et al. | |
| 8,993,627 B2 | 3/2015 | Goldstein | |
| 9,012,674 B1 * | 4/2015 | Neary | C07C 327/34 558/257 |
| 9,034,824 B2 | 5/2015 | Mograbi et al. | |

(Continued)

FOREIGN PATENT DOCUMENTS

| | | |
|---|---|---|
| AU | 2002333018 | 4/2003 |
| CA | 2461703 C | 4/2011 |

(Continued)

OTHER PUBLICATIONS

Banaclocha, M.M., "Therapeutic potential of N-acetylcysteine in age-related mitochondrial neurodegenerative diseases," *Med. Hypotheses*, 56(4): 472-477 (Apr. 2001).

(Continued)

*Primary Examiner* — Alexander R Pagano
*Assistant Examiner* — Ebenezer O Sackey
(74) *Attorney, Agent, or Firm* — Leydig, Voit & Mayer, Ltd.

(57) ABSTRACT

Novel substituted N-acetyl-L-cysteine (NAC) derivatives and related compounds and methods of using these compounds for the treatment of diseases and/or conditions, including but not limited to diseases and/or conditions of, or involving, the Central Nervous System (CNS), including schizophrenia adrenoleukodystrophy, mitochondrial diseases (e.g. Leigh syndrome, Alpers' disease, and MELAS), Huntington's disease, trichotillomania, HIV-associated neurocognitive disorder, hypoxic-ischemic encephalopathy, drug craving, and drug addiction.

21 Claims, 36 Drawing Sheets

(56) References Cited

U.S. PATENT DOCUMENTS

| | | | |
|---|---|---|---|
| 9,062,086 B2 | 6/2015 | Xie et al. | |
| 9,630,937 B2* | 4/2017 | Neary | C07C 327/34 |
| 10,112,897 B2 | 10/2018 | Neary et al. | |
| 2005/0032708 A1 | 2/2005 | Bush et al. | |
| 2010/0048587 A1 | 2/2010 | Cook et al. | |
| 2010/0234452 A1 | 9/2010 | Mian et al. | |
| 2011/0224156 A1 | 9/2011 | Wolf et al. | |
| 2012/0122793 A1 | 5/2012 | Johnson et al. | |
| 2013/0065961 A1 | 3/2013 | Bush et al. | |
| 2013/0172418 A1 | 7/2013 | Choi et al. | |
| 2014/0030323 A1 | 1/2014 | Arad et al. | |
| 2015/0038586 A1 | 2/2015 | Goldstein | |
| 2015/0133470 A1 | 5/2015 | Neary et al. | |
| 2015/0133544 A1 | 5/2015 | Neary et al. | |
| 2015/0133558 A1 | 5/2015 | Goldstein | |
| 2015/0175559 A1 | 6/2015 | Cook et al. | |
| 2015/0209309 A1 | 7/2015 | Rosenfeld | |
| 2015/0209310 A1 | 7/2015 | Rosenfeld | |
| 2015/0218211 A1 | 8/2015 | Mograbi et al. | |
| 2017/0210716 A1 | 7/2017 | Neary et al. | |

FOREIGN PATENT DOCUMENTS

| | | |
|---|---|---|
| CN | 1233629 C | 12/2005 |
| EP | 0080229 A1 | 6/1983 |
| EP | 0174866 A2 | 3/1986 |
| EP | 1491181 A2 | 12/2004 |
| EP | 1438063 B1 | 5/2010 |
| JP | 2005/508333 T2 | 3/2005 |
| JP | 04684553 B2 | 3/2005 |
| JP | 2010/215646 A2 | 9/2010 |
| WO | WO 1995/017900 A1 | 7/1995 |
| WO | WO 1995/034303 A1 | 12/1995 |
| WO | WO 00/00469 A2 | 1/2000 |
| WO | WO 2003/047499 A2 | 6/2003 |
| WO | WO 2007/042816 A1 | 4/2007 |
| WO | WO 2009/100431 A1 | 8/2009 |
| WO | WO 2009/137827 A2 | 11/2009 |
| WO | WO 2013/016727 A1 | 1/2013 |
| WO | WO 2015/112715 A1 | 7/2015 |

OTHER PUBLICATIONS

Berge et al., "Pharmaceutical Salts," *J. Pharm. Sci.*, 66(1): 1-19 (Jan. 1977).
Berk et al., "The promise of N-acetylcysteine in neuropsychiatry," *Trends Pharmacol. Sci.*, 34(3): 167-177 (Mar. 2013).
Berman et al., "N-acetylcysteine prevents loss of dopaminergic neurons in the EAAC1-/- mouse," *Ann. Neurol.*, 69(3): 509-520 (Mar. 2011).
Bridges et al., "Thinking outside the cleft to understand synaptic activity: contribution of the cystine-glutamate antiporter (System Xc-) to normal and pathological glutamatergic signaling" *Pharmacol. Rev.*, 64(3): 780-802 (Jul. 2012).
Bridges et al., "System xc-cystine/glutamate antiporter: an update on molecular pharmacology and roles within the CNS," *Br. J. Pharmacol.*,165(1): 20-34 (Jan. 2012).
Cacciatore et al., "Prodrug approach for increasing cellular glutathione levels," *Molecules*, 15: 1242-1264 (2010).
Chowdhury et al., "Cobalt Assisted Cleavage of S—S Bonds and a Base-Free Synthesis of Mercapturic Acids," *Tetrahedron Letters*, 38(12): 2149-2152 (1997).
Crankshaw et al., "Double-prodrugs of L-cysteine: Differential protection against acetaminophen-induced hepatotoxicity in mice," *J. Biochem. Mol. Toxicol.*, 16(5): 235-244 (Nov. 18, 2002).
Dean et al., "A Role for Glutathione in the Pathophysiology of Bipolar Disorder and Schizophrenia? Animal Models and Relevance to Clinical Practice," *Curr. Med. Chem.*, 16(23): 2965-2976 (Aug. 2009).
El-Gendy et al., "[alpha]-substitution effects on the ease of S—N-acyl transfer in aminothioesters," *Chem. Bio. Drug Design*, 81(5): 577-582 (Apr. 24, 2013).

European Patent Office, International Search Report and Written Opinion in International Patent Application PCT/US2014/064581 (dated Jan. 21, 2015).
Ferrari et al., "N-acetylcysteine (D- and L-stereoisomers) prevents apoptotic death of neuronal cells," *J. Neurosci.*, 15(4): 2857-2866 (Apr. 1995).
Fourcade et al., "Early oxidative damage in neurodegeneration Underlying X-adrenoleukodystrophy," *Hum. Mol. Genet.*, 17(12): 1762-1773 (Jun. 15, 2008).
Frederick et al., "Dysregulation of system xc(-) expression induced by mutant huntingtin in a striatel neuronal cell line and in R6/2 mice," *Neurochem. Int.*, 76: 59-69 (Oct. 2014).
Gilman et al., "Diverse types of genetic variation converge on functional gene networks involved in schizophrenia," *Nat Neurosci.*, 15(12): 1723-1738 (Dec. 2012).
Giustarini et al., "N-Acetylcysteine ethyl ester (NACET): A novel lipophilic cell-permeable cysteine derivative with an unusual pharmacokinetic feature and remarkable antioxidant potential," *Biochemical Pharmacology*, 84: 1522-1533 (2012).
Grant et al., "N-Acetylcysteine, a Glutamate Modulator, in the Treatment of Trichotillomania: a double-blind, placebo-controlled study," *Arch. Gen. Psychiatry*, 66(7): 756-763 (Jul. 2009).
Ibrahim et al., "Macrocyclic peptoids by selective s-acylation of cysteine esters," *Synthesis*, 45(6): 767-772 (Feb. 2, 2013).
Kahns et al., "Prodrugs as drug delivery systems. 107. Synthesis and chemical and enzymatic hydrolysis kinetics of various mono- and diester prodrugs of N-acetylcysteine," *International Journal of Pharmaceutics*, 62: 193-205 (1990).
Katritzky et al., "Chemical Ligation of S-Scylated Cysteine Peptides to Form Native Peptides via 5-, 11-, and 14-Membered Cyclic Transition States," *J. Org. Chem.*, 76(1): 85-96 (Dec. 15, 2010).
Katz et al., "Cerebrospinal fluid concentrations of N-acetylcysteine after oral administration in Parkinson's disease," *Parkinsonism and Related Disorders*, 21(5): 500-503 (2015).
Kessler et al., "Prevalence, Severity, and Comorbidity of 12-Month DSM-IV Disorders in the National Comorbidity Survey Replication," *Arch. Gen. Psychiatry*, 62(6): 617-627 (Jun. 2005).
Kumari et al., "Glutamate Induces Mitochondrial Dynamic Imbalance and Autophagy Activation," *Preventive Effects of Selenium*, 7(6): e39382 (Jun. 19, 2012).
Li et al., "Organocatalysis with cysteine derivatives: recoverable and cheap chiral catalyst for direct aldol reactions," *Res. Chem. Inter.*, 38(1): 195-205 (Jun. 15, 2011).
Lobner, D., "Comparison of the LDH and MTT assays for quantifying cell death: validity for neuronal apoptosis?," *J. Neurosci. Methods*, 96(2): 147-152 (Mar. 15, 2000).
Lopez-Erauskin et al., "Antioxidants halt axonal degeneration in a mouse model of X-adrenoleukodystrophy," *Ann. Neurol.*, 70(1): 84-92 (Jul. 2011).
Martinez et al., "N-Acetylcysteine delays age-associated memory impairment in mice: role in synaptic mitochondria," *Brain Res.*, 855(1): 100-106 (Feb. 2000).
Massie et al., "Dopaminergic neurons of system Xc-deficient mice are highly protected against 6-hydroxydopamine-induced toxicity," *FASEB J*, 25(4): 1359-1369 (Dec. 29, 2010).
Mayer et al., "N-Acetyl-L-cysteine is a pluripotent protector against cell death and enhancer of trophic factor-mediated cell survival in vitro," *PNAS USA*, 91(16): 7496-7500 (Aug. 2, 1994).
Miller et al., "Outcomes after allogeneic hematopoietic cell transplantation for childhood cerebral adrenoleukodystrophy: the largest single-institution cohort report," *Blood*, 118(7): 1971-1978 (Aug. 18, 2011).
Peters et al., "Cerebral X-linked adrenoleukodystrophy: the international hematopoietic cell transplantation experience from 1982 to 1999," *Blood*, 104(3): 881-888 (Aug. 1, 2004).
Photaki, "On Cysteine and Cystine Peptides. Part VI. S-acylcysteines in Peptide Synthesis," *Journal of the Chemical Society*, 19: 2687-2689 (1970).
Portelli et al., "Synthesis of N-acetylcysteine compounds," *Il Farmaco, Ed. Sci.*, 31: 767-775 (1976).
Prescott (editor), "Lipid Vesicles as Carriers for Introducing Biologically Active Materials into Cells" (Chapter 4), in *Methods in Cell Biology* (vol. XIV), Academic Press, pp. 33-71 (1976).

(56) References Cited

OTHER PUBLICATIONS

Reyes et al., "Neuronal glutathione content and antioxidant capacity can be normalized in situ by N-acetyl cysteine concentrations attained in human cerebrospinal fluid," *Neurotherapeutics*, 13(1): 217-225 (2016).
Rimaniol et al., "Role of glutamate transporters in the regulation of glutathione levels in human macrophages," *Am. J. Physiol. Cell. Physiol.*, 281(6): C1964-C1970 (Dec. 1, 2001).
Schulz et al., "Glutathione, oxidative stress and neurodegeneration," *Eur. J. Biochem.*, 267(16): 4904-4911 (Aug. 2000).
Still et al., "Rapid chromatographic technique for preparative separations with moderate resolution," *J. Org. Chem.*, 43(14): 2923-2925 (Jul. 1, 1978).
Sunitha et al., "N-Acetylcysteine amide: a derivative to fulfill the promises of N-Acetylcysteine," *Free Radical Research*, 47(5): 357-367 (2013).
Tolar et al., "N-acetyl-L-cysteine improves outcome of advanced cerebral adrenoleukodystrophy," *Bone Marrow Transplant*, 39(4): 211-215 (Feb. 2007).
Uttamsingh et al., "Acylase I-Catalyzed Deacetylation of N-Acetyl-L-cysteine and S-Alkyl-N-acetyl-L-cysteines," *Chem. Res. Toxicol.*, 11(7): 800-809 (1998).
Vazquez-Santiago et al., "Glutamate metabolism and HIV-associated neurocognitive disorders," *J. Neurovirol.*, 20(4): 315-331 (Aug. 2014).
Wang et al., "Redox-sensitive shell cross-linked PEG-polypeptide hybrid micelles for controlled drug release," *Poly. Chem.*, 3(4): 1084 (Jan. 1, 2012).
Wang et al., "N-acetylcysteine reduces lipopolysaccharide-sensitized hypoxic-ischemic brain injury," *Ann. Neurol.*, 61(3): 263-271 (Mar. 2007).
Wu et al., "Separation and quantification of N-acetyl-L-cysteine and N-acetyl-cysteine-amide by HPLC with fluorescence detection," *Biomedical Chromatography*, 20: 415-422 (2006).
Australian Patent Office, First Examination Report in Australian Patent Application No. 2014346591 (dated Feb. 2, 2018).
European Patent Office, First Office Action in European Patent Application No. 14802771.7 (dated Jan. 3, 2018).
European Patent Office, Second Office Action in European Patent Application No. 14802771.7 (dated Nov. 22, 2018).
Japanese Patent Office, First Office Action in Japanese Patent Application No. 2016-528225 (dated Jul. 24, 2018).
Japanese Patent Office, First Office Action in Japanese Patent Application No. 2017-213633 (dated Aug. 28, 2018).
U.S. Appl. No. 14/535,855, filed Nov. 7, 2014.
U.S. Appl. No. 14/535,953, filed Nov. 7, 2014.
U.S. Appl. No. 15/459,840, filed Mar. 15, 2017.

\* cited by examiner

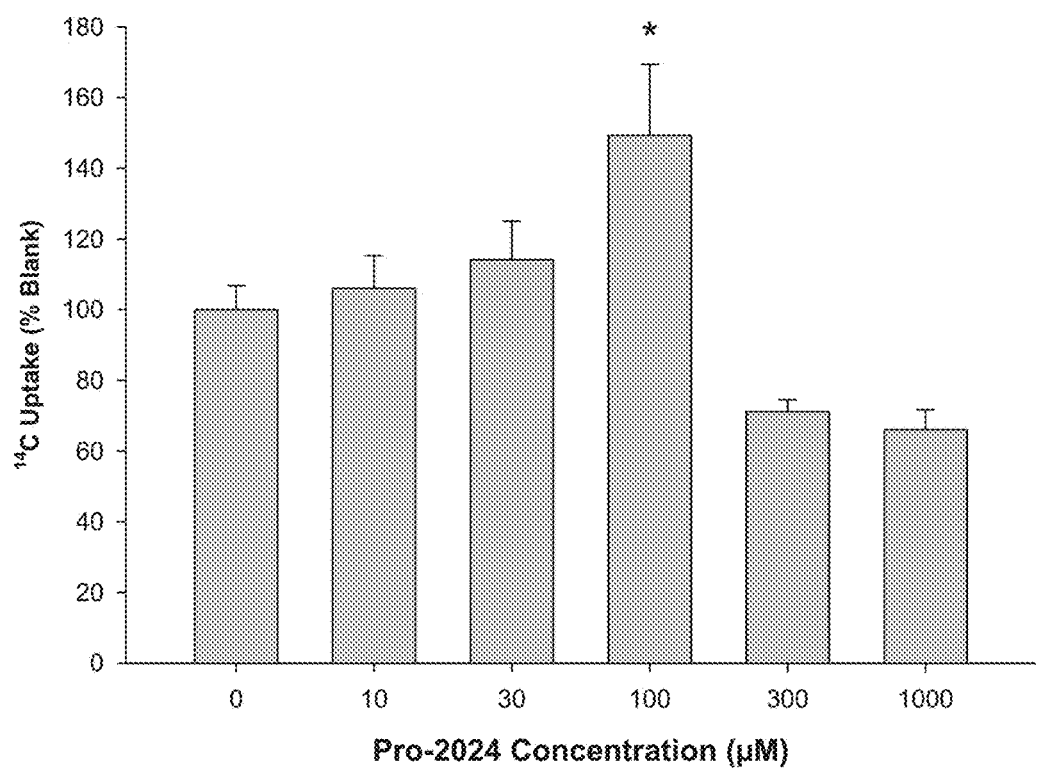

C. Pro-4051 ³H-glutamate release (30 min)

D. Pro-4051 ³H-glutamate release (3 hours)

SUBSTITUTED N-ACETYL-L-CYSTEINE DERIVATIVES AND RELATED COMPOUNDS

CROSS-REFERENCE TO RELATED APPLICATIONS

This application is a continuation of copending U.S. patent application Ser. No. 14/535,855, filed Nov. 7, 2014, which claims the benefit of U.S. Provisional Application 61/902,669, filed Nov. 11, 2013, and U.S. Provisional Application 61/902,052, filed Nov. 8, 2013, the disclosure of each of which is hereby incorporated by reference in its entirety.

FIELD OF THE INVENTION

This invention relates to novel substituted N-acetyl-L-cysteine ("NAC") derivatives and related compounds and methods of using these compounds for the treatment of diseases and/or conditions, including but not limited to diseases and/or conditions of, or involving, the Central Nervous System (CNS), including schizophrenia adrenoleukodystrophy, mitochondrial diseases (e.g. Leigh syndrome, Alpers' disease, and MELAS), Huntington's disease, trichotillomania, HIV-associated neurocognitive disorder, hypoxic-ischemic encephalopathy, drug craving, and drug addiction.

BACKGROUND OF THE INVENTION

Schizophrenia is a debilitating disorder afflicting 1% of the world's population. The development of effective medications to treat schizophrenia relies on advances in characterizing the underlying pathophysiology. Chlorpromazine and other phenothiazines are considered first generation antipsychotics (termed "typical antipsychotics") useful in the treatment of schizophrenia.

Adrenoleukodystrophy, or X-linked adrenoleukodystrophy, is an inherited life-threatening metabolic rare disease. It primarily affects myelination throughout the nervous system, the adrenal cortex, and the Leydig cells in the testes where very-long chain fatty acids accumulate. The adrenoleukodystrophy patient population is heterogeneous, with clinical phenotypes that include progressive neurodegenerative decline leading to vegetative state in children (childhood cerebral X-linked adrenoleukodystrophy). Treatments for adrenoleukodystrophy are include hematopoietic stem cell transplant, which results in a high-survival rate (92% 5-year survival; Peters et al., "Cerebral X-linked adrenoleukodystrophy: the international hematopoietic cell transplantation experience from 1982 to 1999," Blood, 104: 881-888 (2004)); however, this treatment is limited to and effective with only a small adrenoleukodystrophy subpopulation, with success typically coming when it is performed in the early stages of the disease.

Adrenoleukodystrophy patients have one or more mutations to the ABCD1 gene, which encodes the peroxisomal ATP-binding cassette transporter. Subsequently, very-long chain fatty acids build up in affected cells, leading to oxidative stress and eventually metabolic failure resulting in cell death, features common to human patients and animal models (Fourcade, S, et al. "Early oxidative damage in neurodegeneration Underlying X-adrenoleukodystrophy," Human Molecular Genetics, 17: 1762-1773 (2008); López-Erauskin, J, et al., "Antioxidants halt axonal degeneration in a mouse model of X-adrenoleukodystrophy," Annals of Neurology, 70: 84-92 (2011)).

Antioxidant therapy is a promising therapy for the treatment of adrenoleukodystrophy and other diseases that involve oxidative stress. At the cellular level, antioxidants have been demonstrated to normalize biomarkers of oxidative stress. N-acetylcysteine ("NAC") is a prodrug of cysteine, which serves as the limiting reagent in the synthesis of glutathione, the body's major antioxidant. When given as an adjuvant therapy to hematopoietic stem cell transplant in advanced stage childhood cerebral X-linked adrenoleukodystrophy patients, patient survival outcome greatly improves with NAC treatment (Miller, W, et al., "Outcomes after allogeneic hematopoietic cell transplantation for childhood cerebral adrenoleukodystrophy: the largest single-institution cohort report," Blood, 118: 1971-1978 (2011); Tolar, J, et al., "N-acetyl-L-cysteine improves outcome of advanced cerebral adrenoleukodystrophy." Bone Marrow Transplant, 39: 211-215 (2007)). However, brain penetrance is low and the long-term risks and benefits remain unknown.

Inherited mitochondrial diseases (e.g. Leigh syndrome, Alpers' disease, and MELAS) affecting the CNS are highly variable, and often result in the progressive loss, or dysfunction, of neurons or neuroglial cells. In many cases, the pathogenesis is a result of disruption of mitochondrial respiratory chain processes, which can then increase the generation of reactive oxidative species (ROS), due to mutations in mitochondrial or nuclear DNA. Antioxidant therapy, specifically N-acetylcysteine, acts to decrease ROS and increases glutathione levels, which concomitantly increase cell survival and function.

A range of other diseases share common pathophysiology with abnormal glutamate signaling and heightened levels of oxidative stress, particularly with System $x_c$-, a glutamate-cystine antiporter. Therefore, by engaging a single target, e.g. System $x_c$-, which is at the junction of two distinct metabolic pathways, NAC, NAC derivatives and related molecules, may effectively treat these wide-ranging, and seemingly unrelated, diseases and disorders. This has been partially demonstrated in clinical study with NAC treatment of trichotillomania (Grant, J E, et al., "N-Acetylcysteine, a Glutamate Modulator, in the Treatment of Trichotillomania," Arch Gen Psychiatry, 66: 756-763 (2009)). System $x_c$-, NAC, and disturbances in glutamate signaling and oxidative stress are also linked to other diseases that include, but are not limited to, Huntington's disease (Frederick, N M, et al., "Dysregulation of system xc(-) expression induced by mutant huntingtin in a striatal neuronal cell line and in R6/2 mice," Neurochem. Int., 2014; 76: 59-69), hypoxic-ischemic encephalopathy (Wang, X, et al., "N-acetylcysteine reduces lipopolysaccharide-sensitized hypoxic-ischemic brain injury," Ann. Neurol., 61: 263-271 (2007)), HIV-associated neurocognitive disorder (Vázquez-Santiago, F J, et al., "Glutamate metabolism and HIV-associated neurocognitive disorders," J. Neurovirol., 20: 315-331 (2014)).

Schizophrenia may be associated with abnormal glutamate signaling and diminished glutathione levels. Impaired cystine-glutamate antiporter activity can lead to increased oxidative stress and depleted glutathione, as well as abnormal glutamate neurotransmission, synaptic connection, and gene expression, all of which are observed in schizophrenia. In addition, impaired cystine-glutamate antiporter activity and faulty glutamate neurotransmission bear on the issue of uncontrolled drug use, i.e., drug addiction.

Cysteine prodrugs, such as NAC, drive cystine-glutamate exchange by apparently elevating extracellular cystine levels, thereby creating a steep cystine concentration gradient.

However, alternatives to NAC are needed. NAC undergoes extensive first pass metabolism requiring the usage of high doses that limit the utility of the drug and, potentially, increase the chances of side effects due to the buildup of metabolized by-products. The compounds of the present invention are designed to substantially avoid the problem of first pass metabolism and therefore exhibit increased efficacy as compared to NAC and other prior cysteine prodrugs. In addition, NAC demonstrates poor CNS penetration due to an inability to cross the blood brain barrier.

Accordingly, there is a need for novel compounds that would have a reduced incidence of problems associated with NAC. The compounds of the present invention are designed to substantially avoid the problems of first pass metabolism and poor CNS bioavailability, thereby exhibiting increased efficacy as compared to NAC and other prior cysteine prodrugs.

SUMMARY OF THE INVENTION

In one aspect, the present invention is directed to a compound of formula I:

where $R_2$ is selected from the group consisting of: $NH_2$, $(C_{1-8}$ alkyl)O—, and OH.

In one embodiment, any one of $C_2$ through $C_7$ in the alkyl chain can be substituted with either nitrogen or oxygen.

In a preferred embodiment $R_2$ is t-butyl-O— or $(CH_3)(CH_2)O$—, $R_3$ is selected from the group consisting of:

$R_4$ is selected from the group consisting of: H and

In particular, the invention provides the following compounds:

-continued

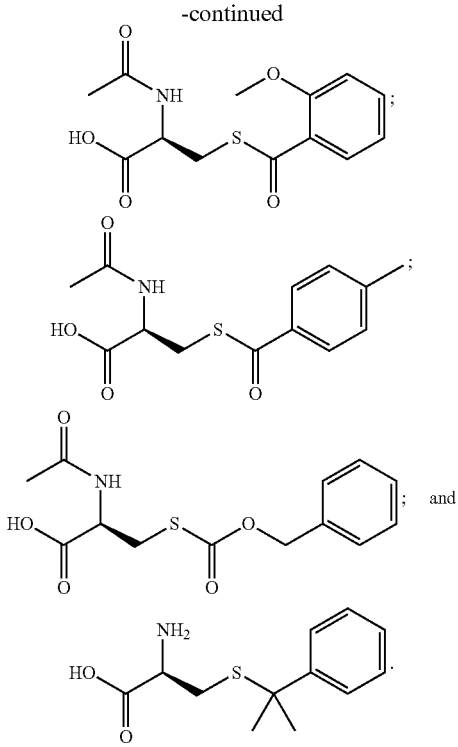

In another aspect, the present invention is directed to a compound of formula II:

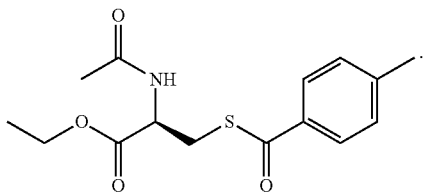

II

The invention also encompasses pharmaceutically acceptable salts, esters or prodrugs of the provided compounds.

In another aspect, the invention is directed to a method of treating a disease or condition in a subject comprising administering to the subject a therapeutically effective amount of a compound of any of Formulas I-II or a pharmaceutically acceptable salt, ester or prodrug thereof. The preferred route of administering to the subject is via oral delivery. Preferably, diseases or conditions treatable with the compounds of the present invention are related to the CNS.

In a preferred embodiment, the disease is schizophrenia.

In another aspect, the invention provides a method of treating drug craving in a subject comprising administering to the subject a therapeutically effective amount of a compound of any of Formulas I-II or a pharmaceutically acceptable salt, ester or prodrug thereof. The preferred route of administering to the subject is via oral delivery.

The invention further encompasses pharmaceutical compositions containing a compound of any of Formulas I-II or a pharmaceutically acceptable salt, ester or prodrug thereof in combination with a pharmaceutically-acceptable carrier.

Methods of formulating/manufacturing such pharmaceutical compositions (alternatively termed "medicaments") for the treatment of a disease or condition in a subject are also within the invention's scope.

BRIEF DESCRIPTION OF THE DRAWINGS

FIG. 3 is a graphical representation of the $^{14}$C-cystine uptake by Pro-2024 as a percentage of the control.

FIG. 15 is a graphical representation of the amount of intracellular cysteine for Pro-4051a.

DETAILED DESCRIPTION OF THE INVENTION

Figure 1A:
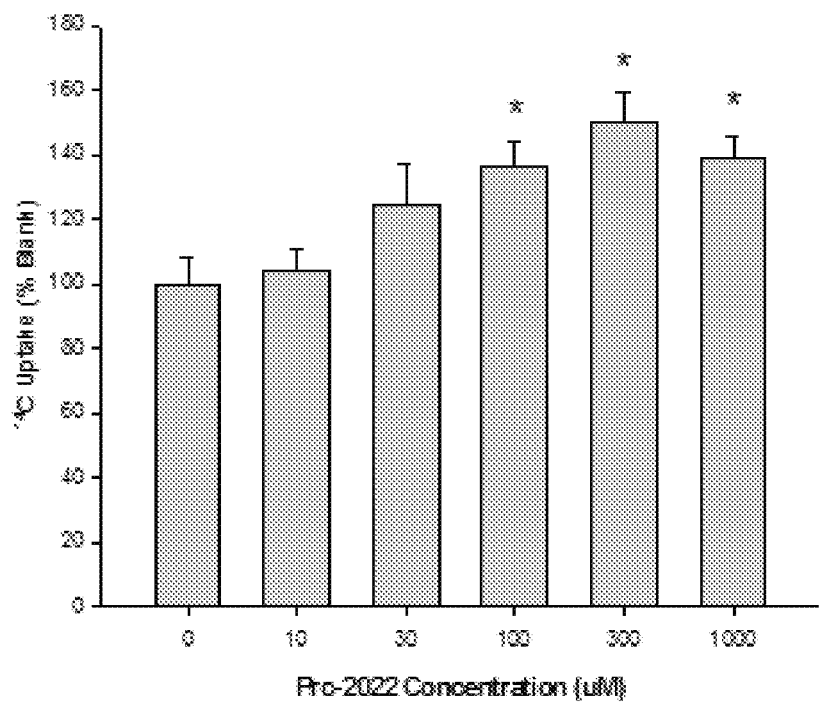
FIGS. 1A-1D are graphical representations of the $^{14}$C-cystine uptake and $^3$H-glutamate release by Pro-2022 as a percentage of the control.
Figure 1B:
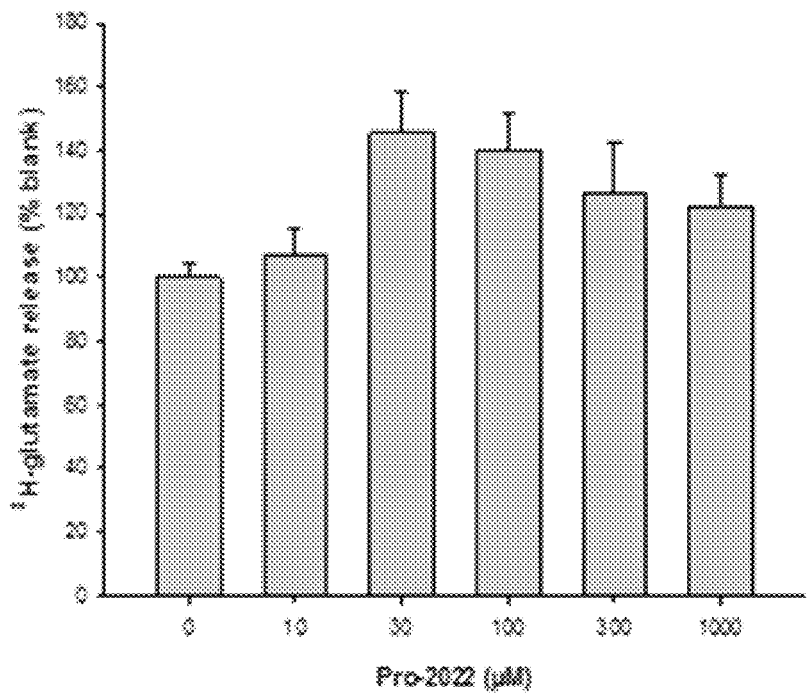
Figure 1C:
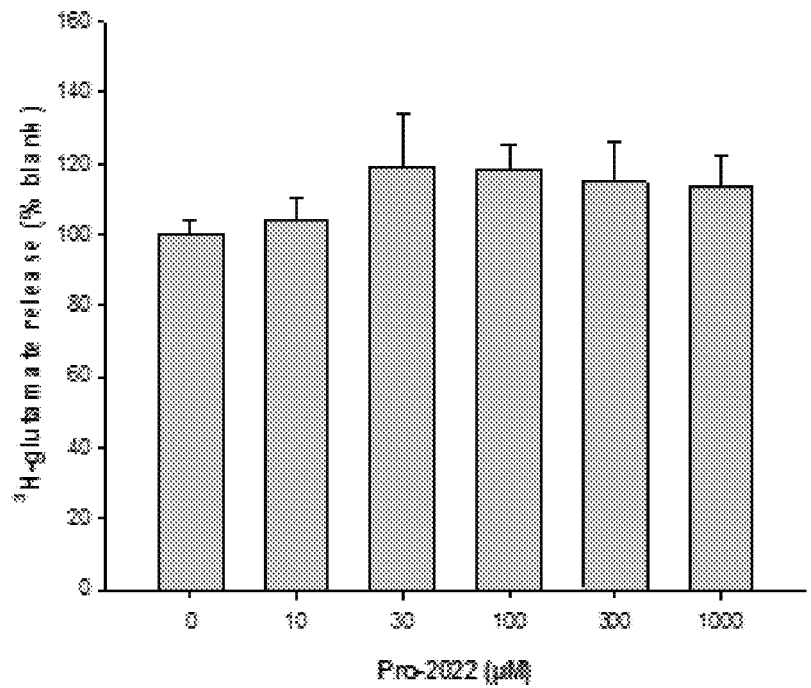
Figure 1D:
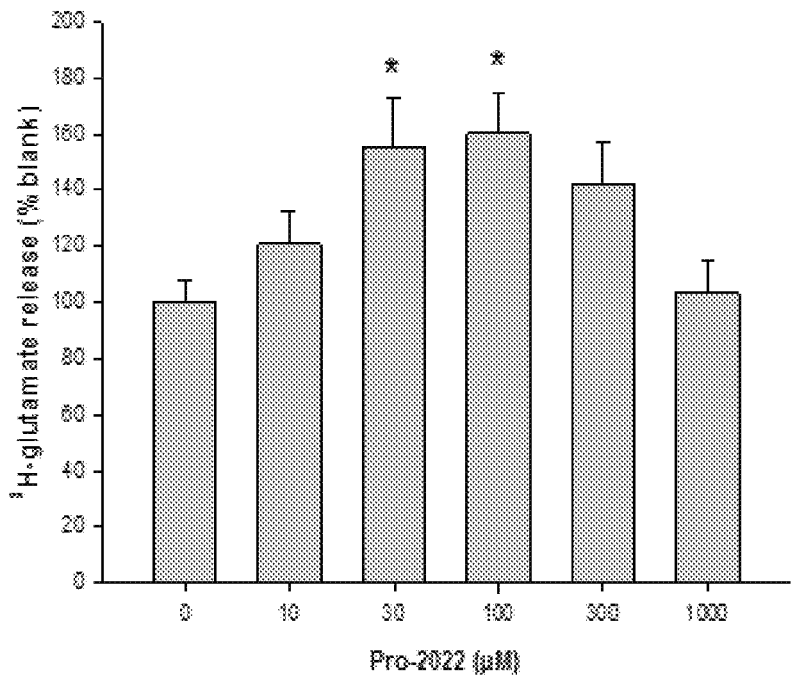
Figure 2A:
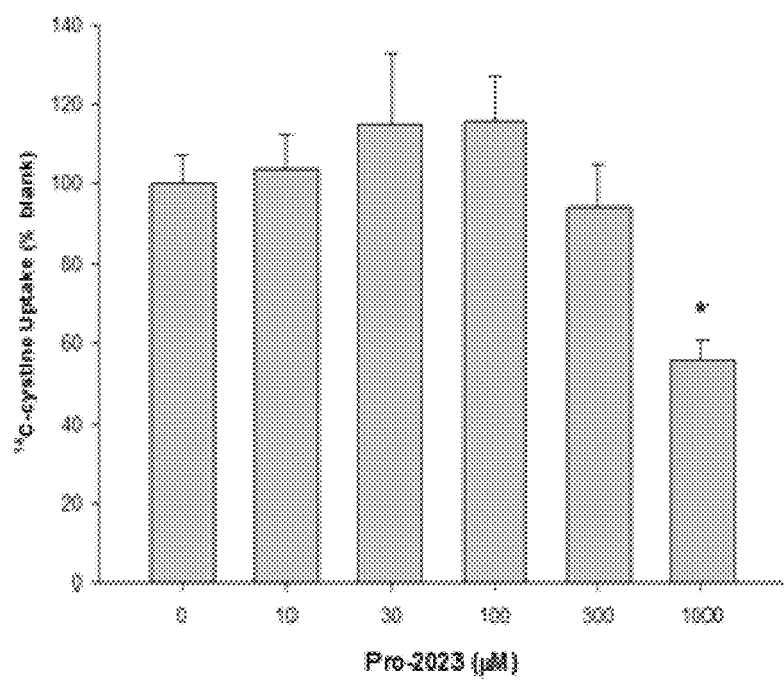
FIGS. 2A-2D are graphical representations of the $^{14}$C-cystine uptake and $^3$H-glutamate release by Pro-2023 as a percentage of the control.
Figure 2B:
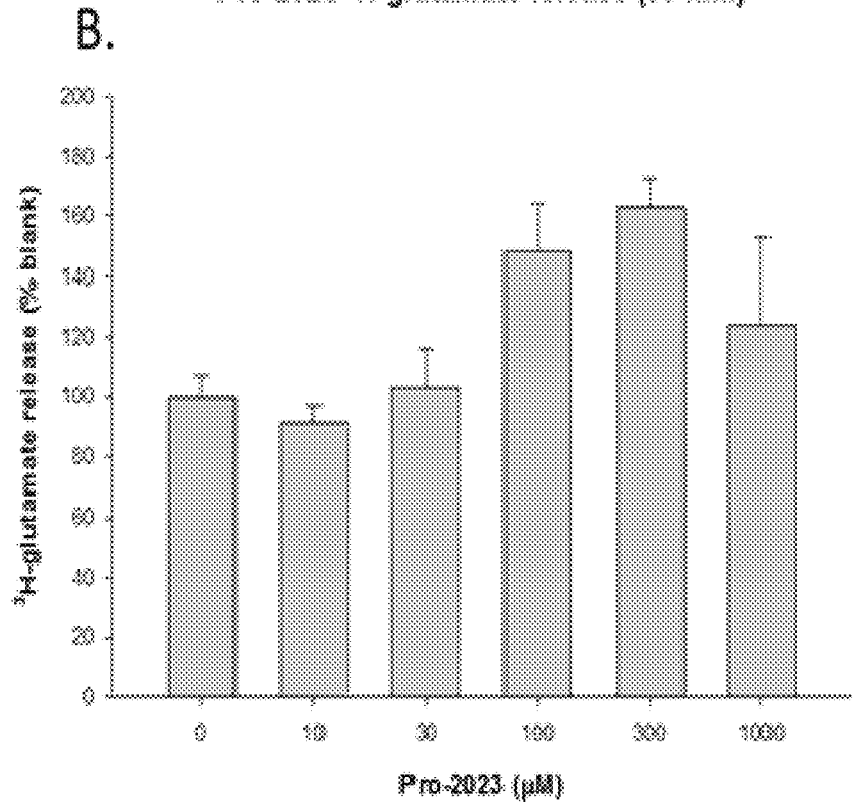
Figure 2C:
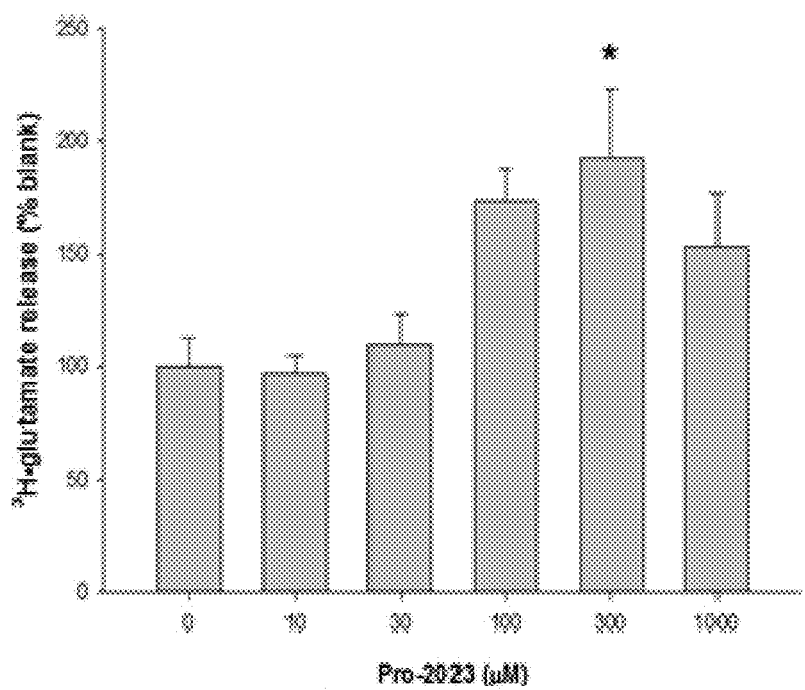
Figure 2D:
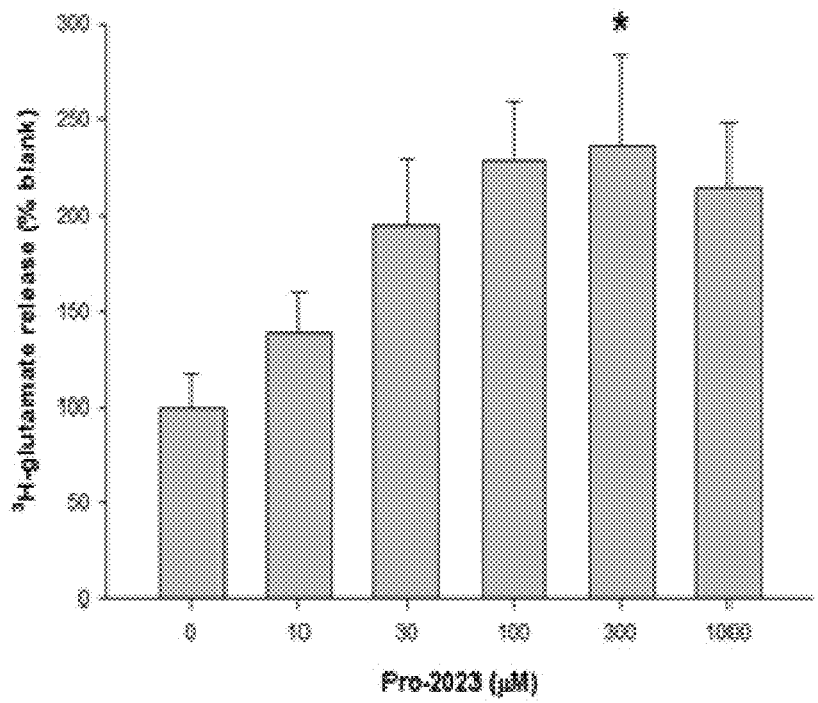
Figure 4:
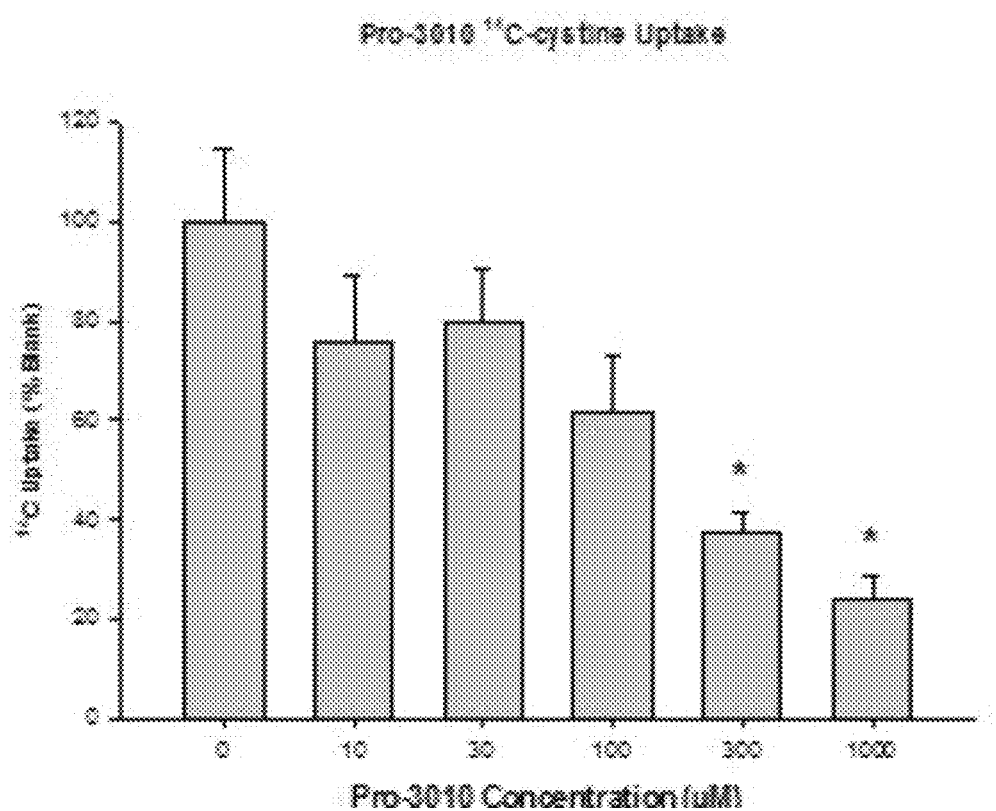
FIG. 4 is a graphical representation of the $^{14}$C-cystine uptake by Pro-3010 as a percentage of the control.
Figures 5A, 5B:
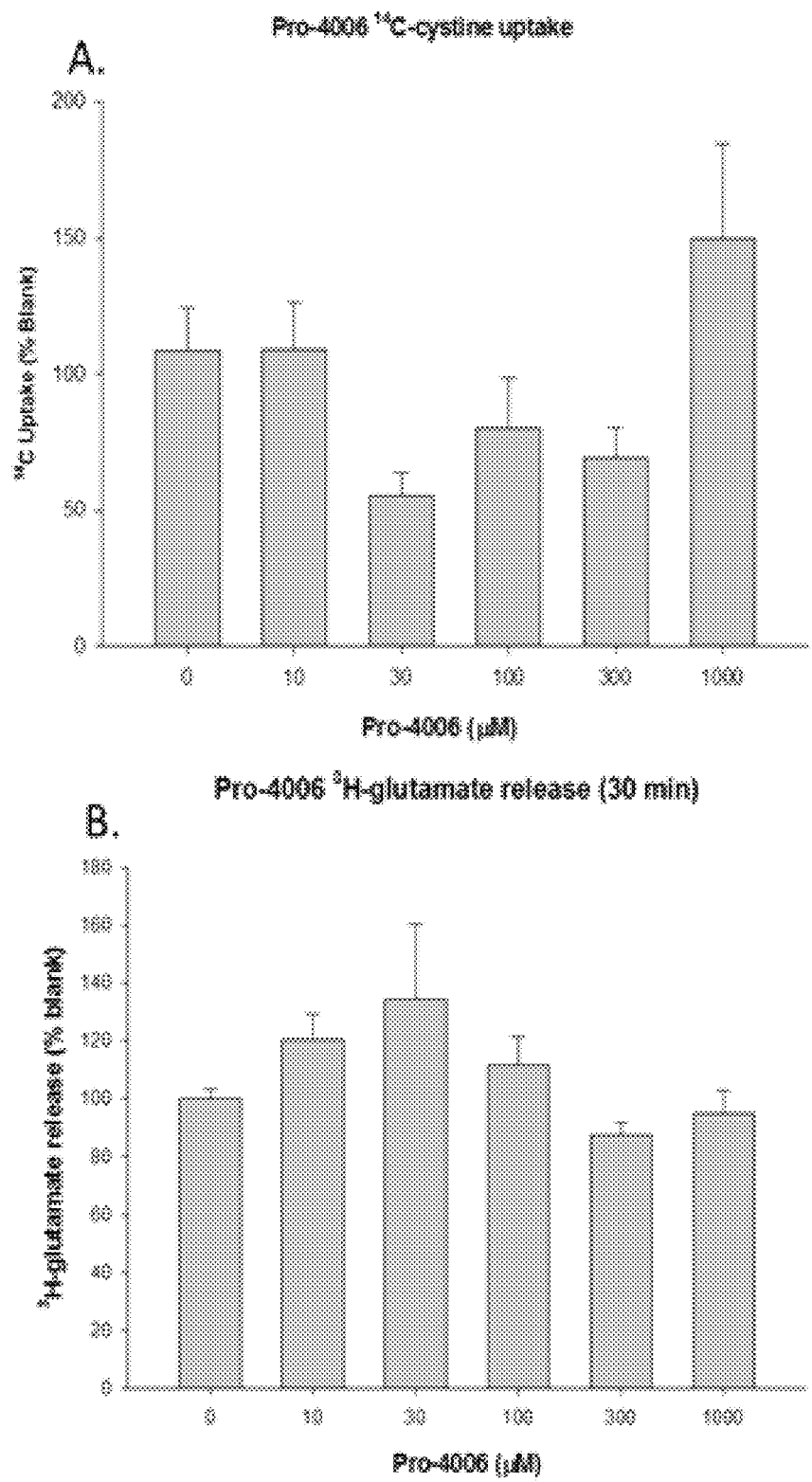
FIGS. 5A-5D are graphical representations of the $^{14}$C-cystine uptake and $^3$H-glutamate release by Pro-4006 as a percentage of the control.
Figure 5C:
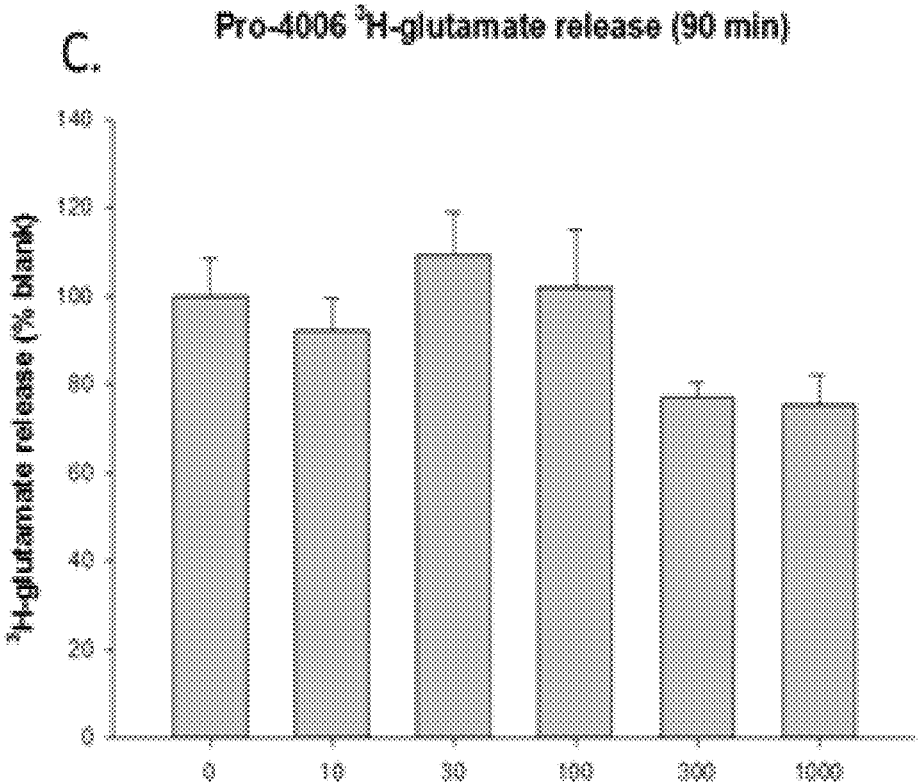
Figure 5D:
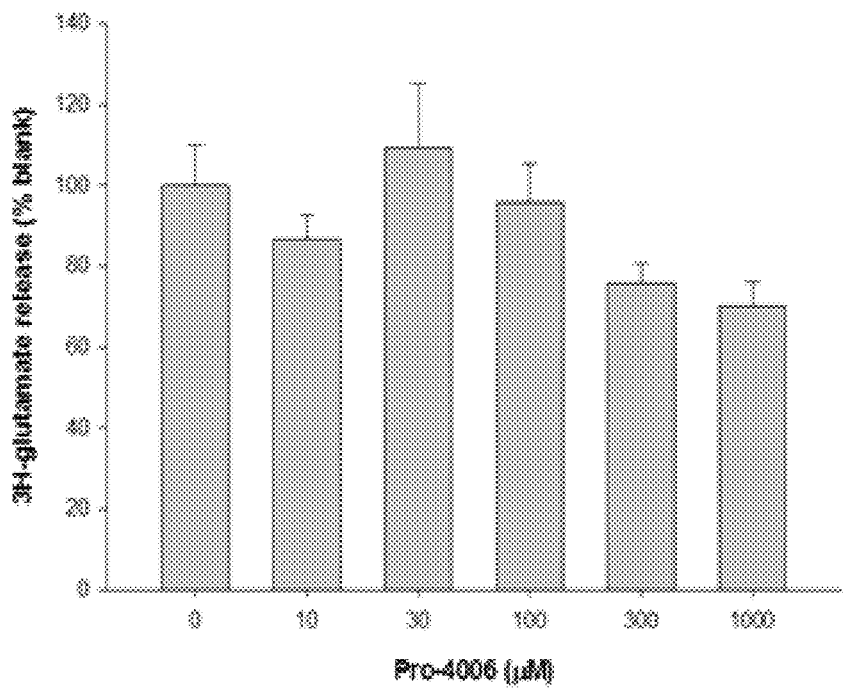
Figures 6A, 6B:
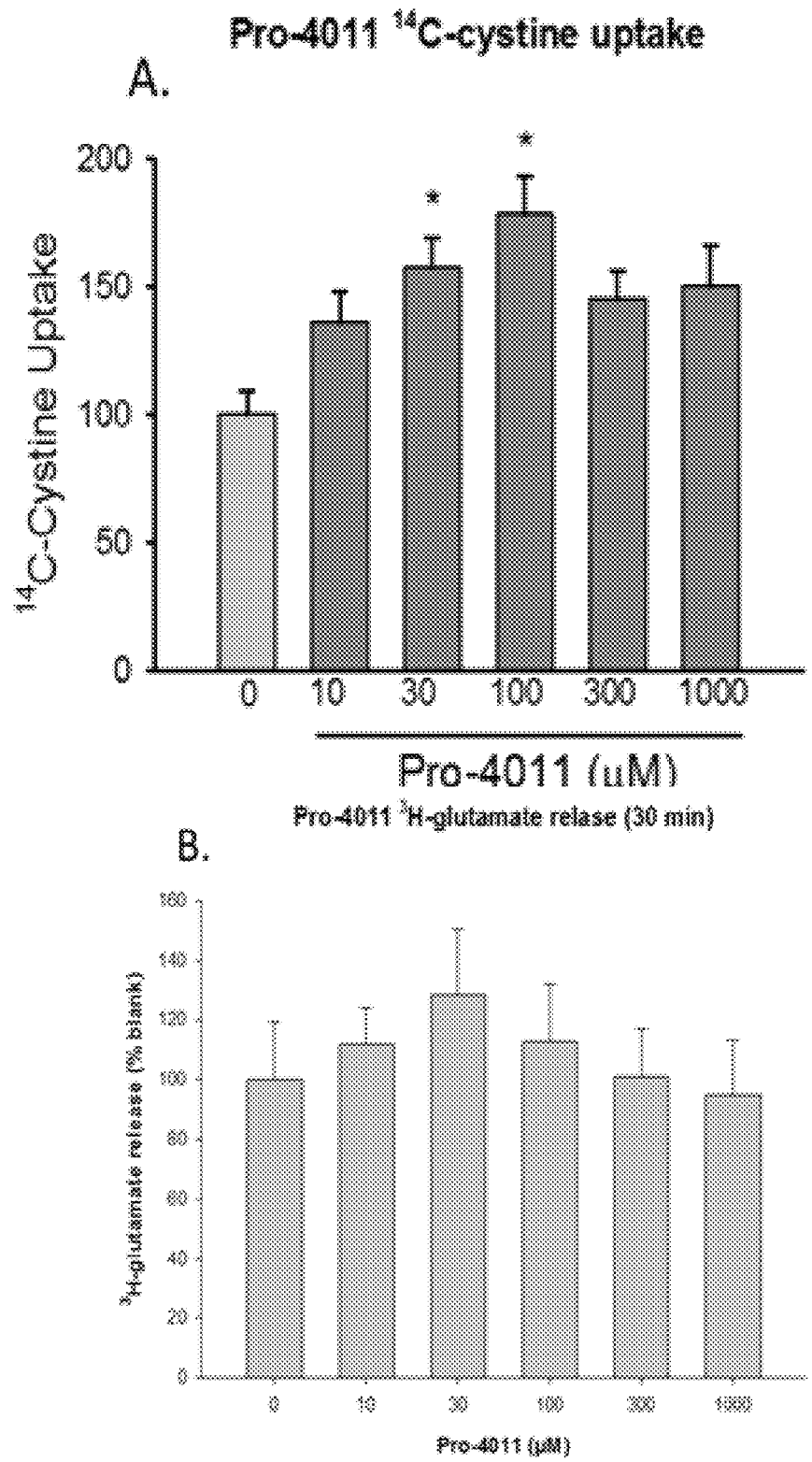
FIGS. 6A-6D are graphical representation of the $^{14}$C-cystine uptake and $^3$H-glutamate release by Pro-4011 as a percentage of the control.
Figure 6C:
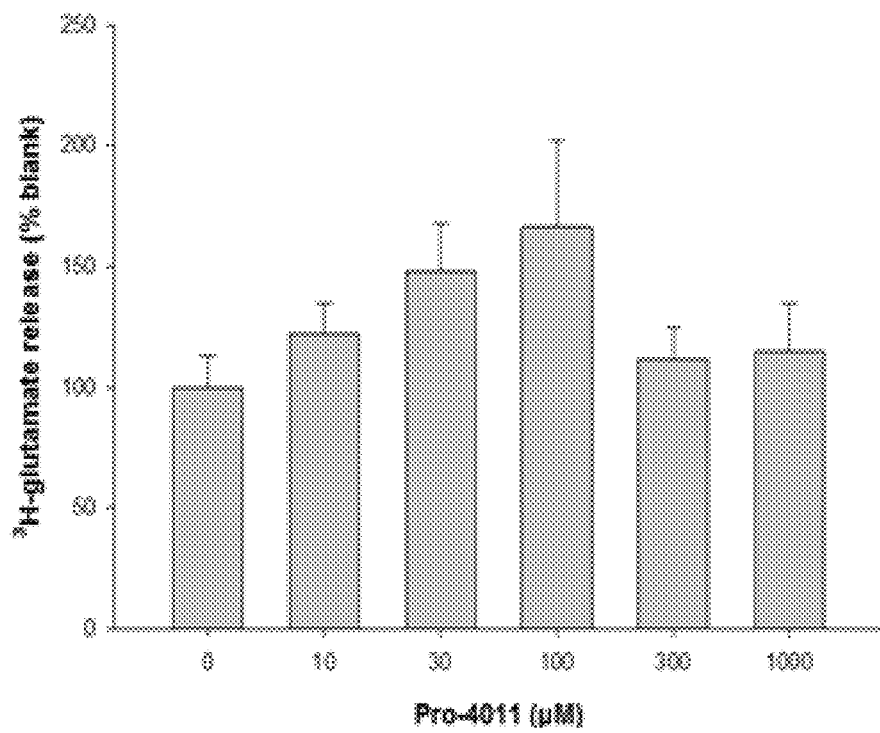
Figure 6D:
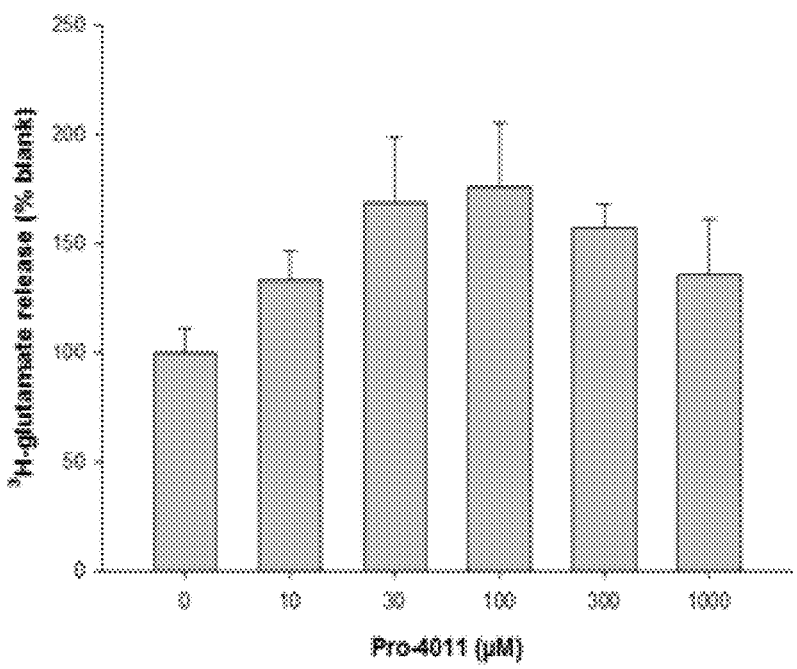
Figures 7A, 7B:
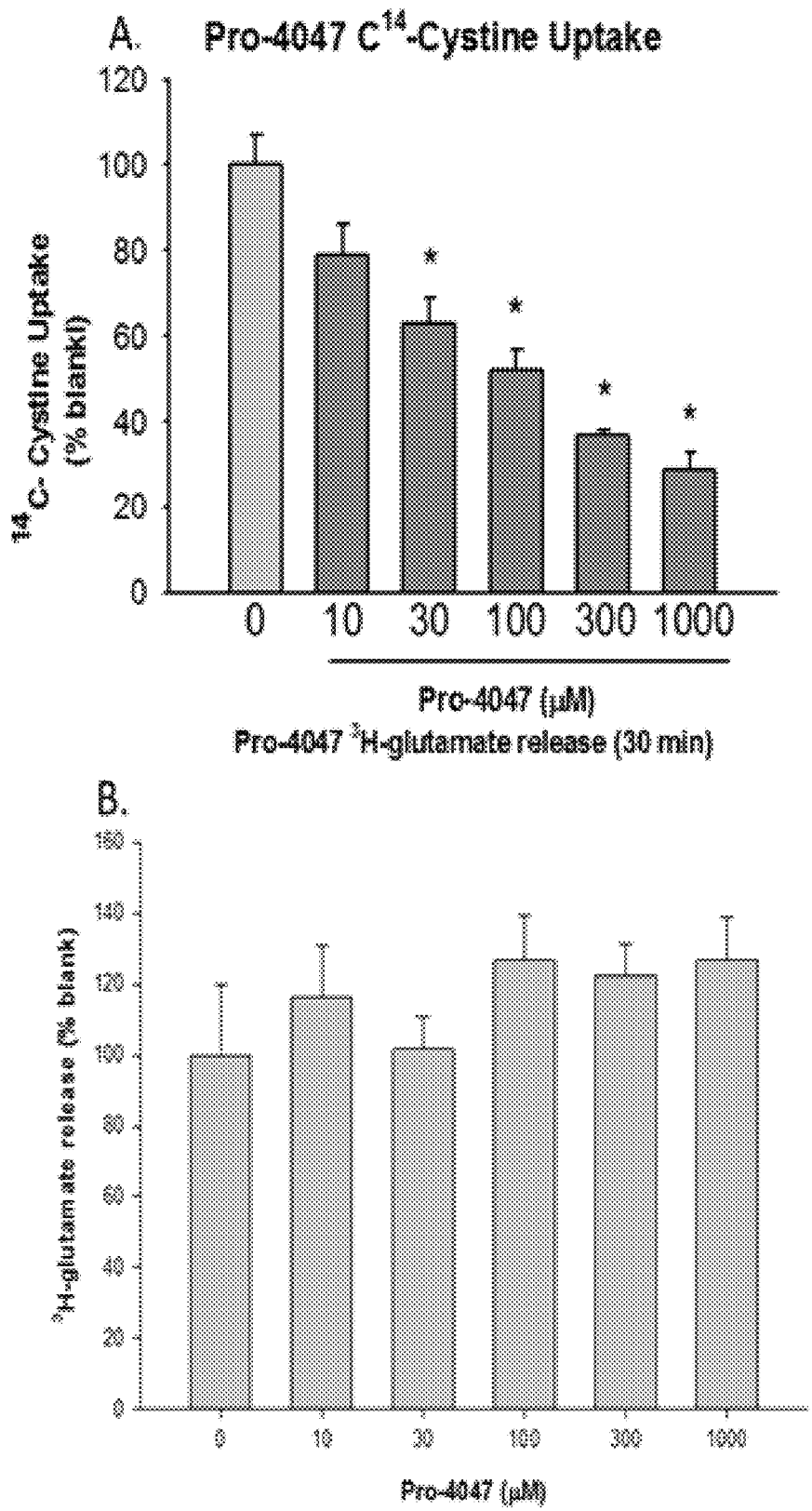
FIGS. 7A-7D are graphical representations of the $^{14}$C-cystine uptake and $^3$H-glutamate release by Pro-4047 as a percentage of the control.
Figure 7C:
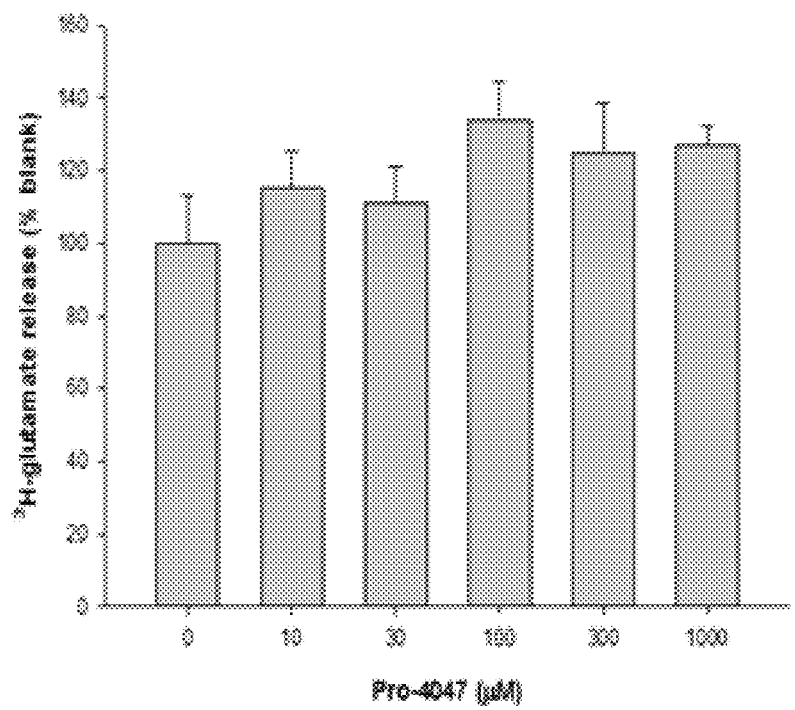
Figure 7D:
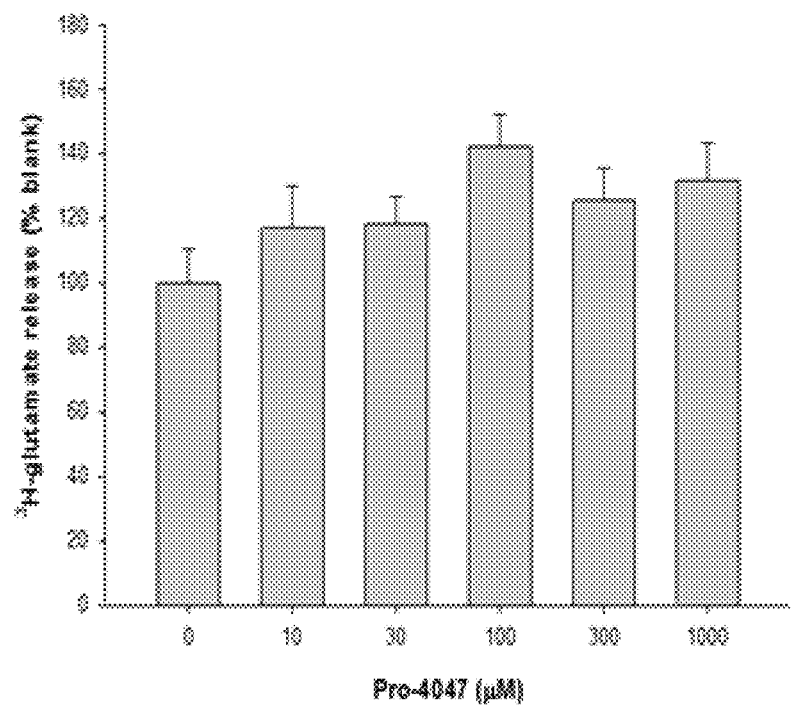
Figure 8A:
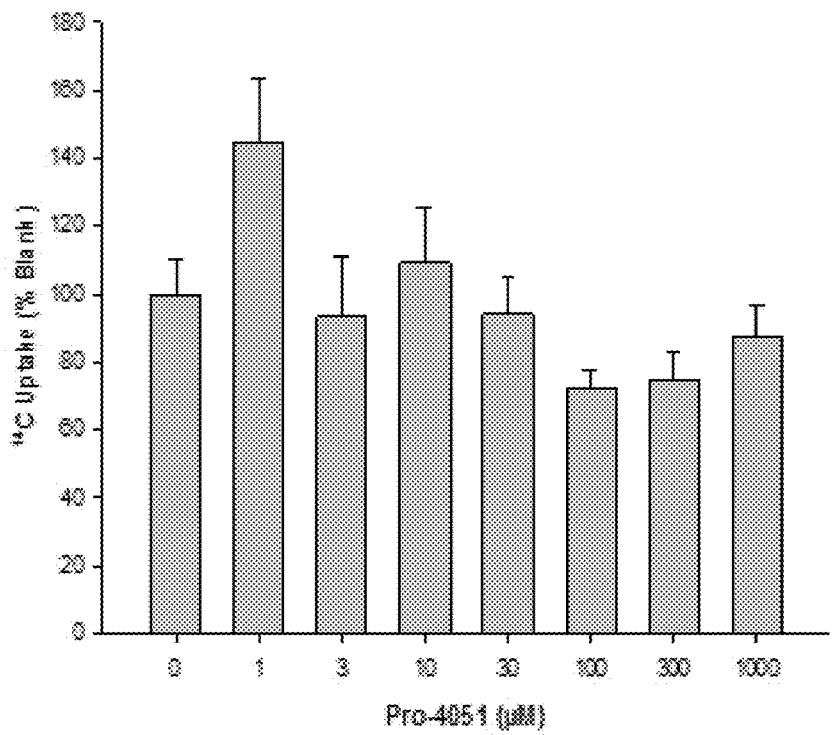
FIGS. 8A-8D are graphical representation of the $^{14}$C-cystine uptake and $^3$H-glutamate release by Pro-4051 as a percentage of the control.
Figure 8B:
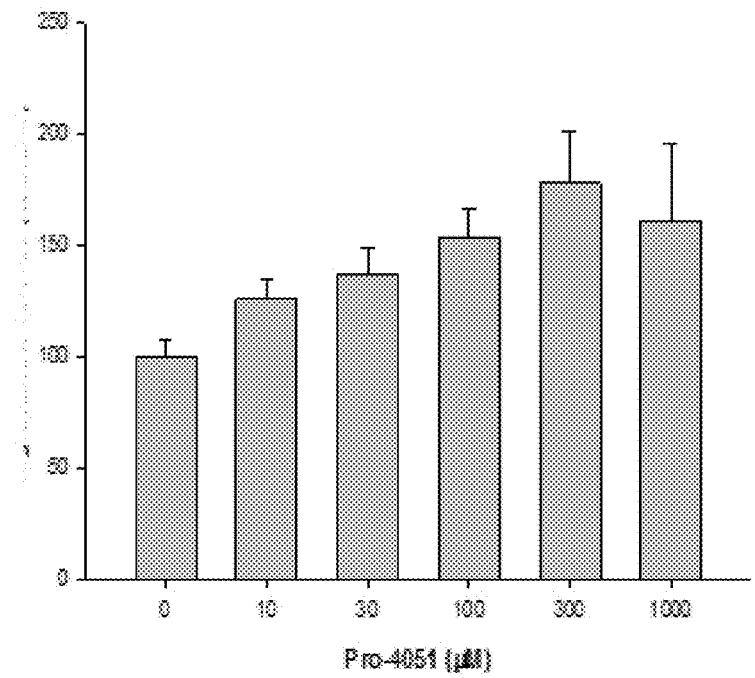
Figure 8C:
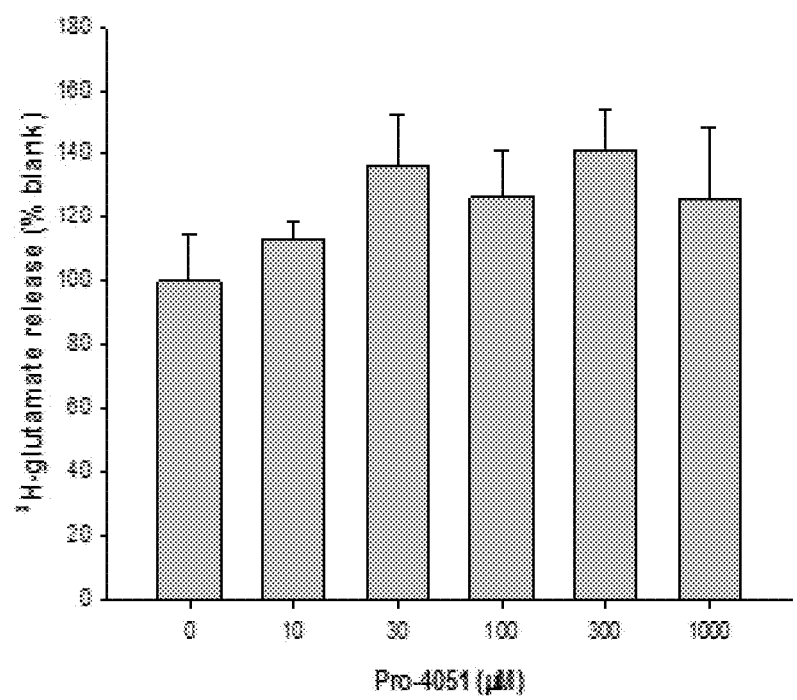
Figure 8D:
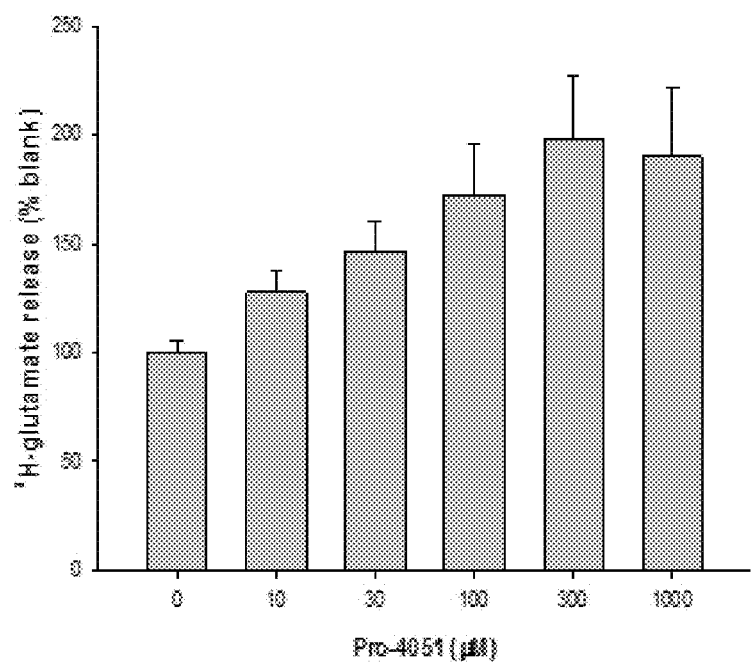
Figure 9A:
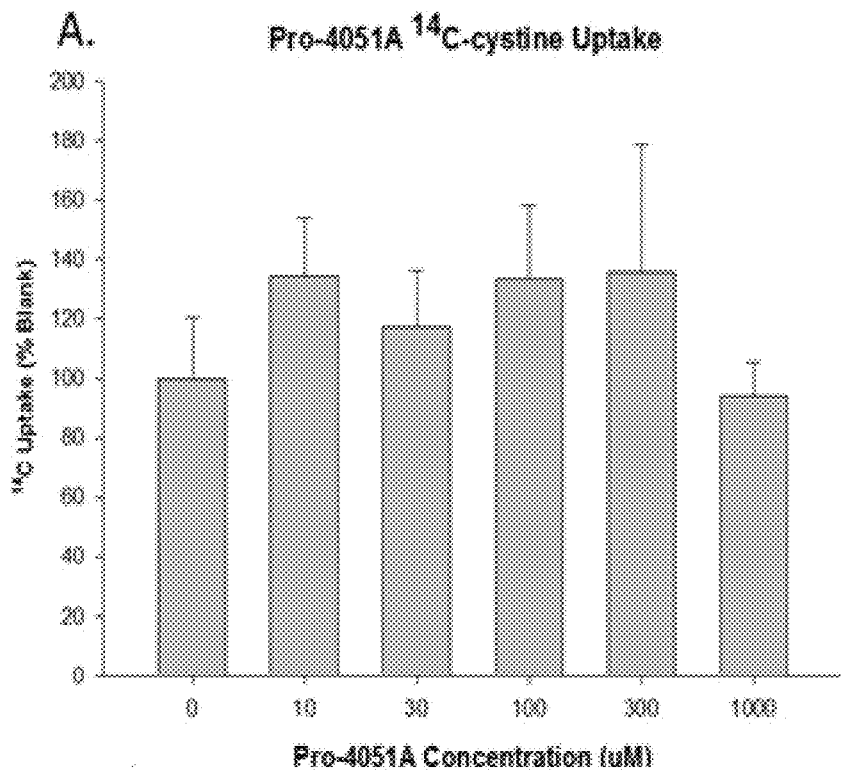
FIGS. 9A-9D are graphical representation of the $^{14}$C-cystine uptake and $^3$H-glutamate release by Pro-4051a as a percentage of the control.
Figure 9B:
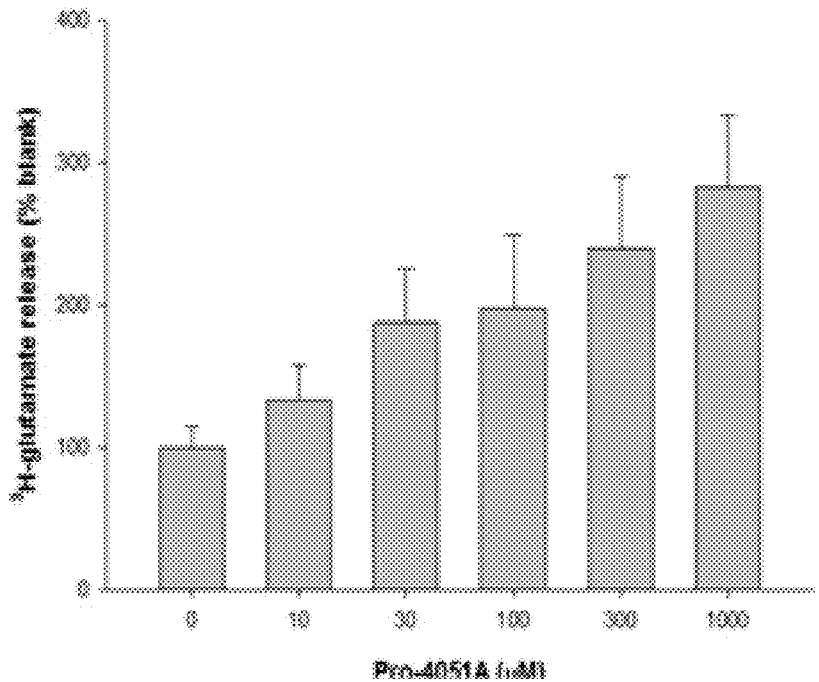
Figure 9C:
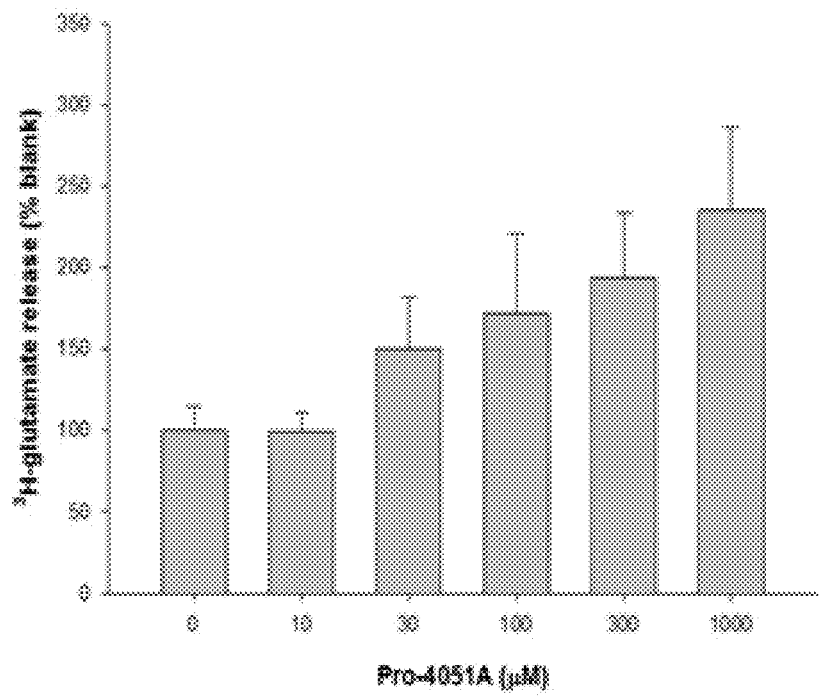
Figure 9D:
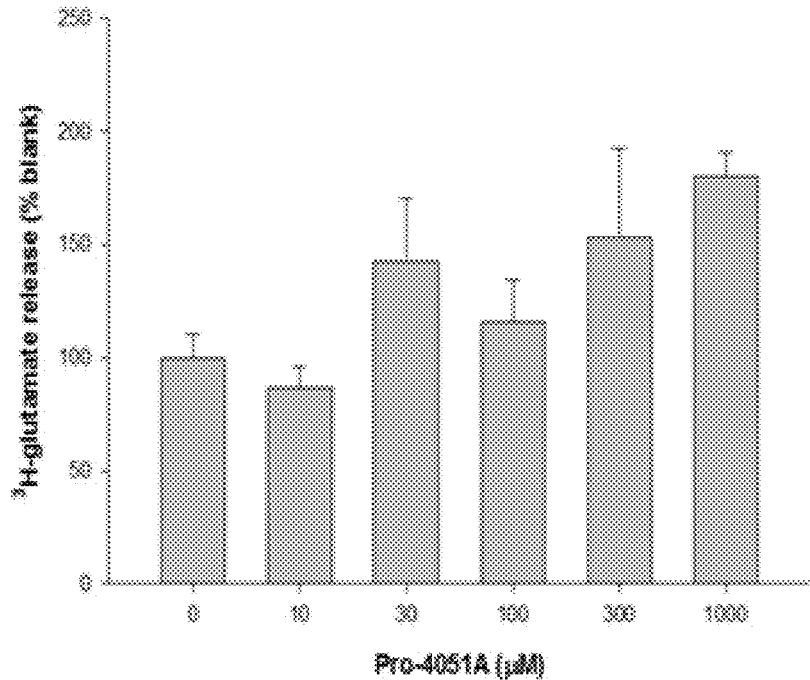

The following definitions are used, unless otherwise described.

The term "prodrug" refers to compounds, including monomers and dimers of the compounds of the invention, which have cleavable groups and become under physiological conditions compounds which are pharmaceutically active in vivo.

The term "ester" refers to compounds having a generic structure of $RCO_2R'$, where R and R' are the organic parts of the carboxylic acid and alcohol respectively.

The term "subject" includes mammals. Mammals include but are not limited to humans. The terms "patient" and "subject" are used interchangeably.

The term "therapeutically effective amount" means the amount of a compound that, when administered to a subject for treating a disease or disorder, is sufficient to effect such treatment for the disease or disorder. The "therapeutically effective amount" can vary depending on the compound, the disease or disorder and its severity, and the age, weight, etc., of the subject to be treated.

The terms "treating" or "treatment" of any disease or disorder refer, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder, or even preventing the same.

The term "alkyl" is intended to mean a straight chain or branched aliphatic group having from 1 to 12 carbon atoms, alternatively 1-8 carbon atoms, and alternatively 1-6 carbon atoms. In some embodiments, the alkyl groups have from 2 to 12 carbon atoms, alternatively 2-8 carbon atoms and alternatively 2-6 carbon atoms. Examples of alkyl groups include, without limitation, methyl, ethyl, propyl, isopropyl, butyl, isobutyl, sec-butyl, tert-butyl, pentyl, hexyl and the like.

In general, unless indicated otherwise, a chemical group referred to anywhere in the specification can be optionally substituted.

In another aspect, the present invention is directed to compounds of formula I:

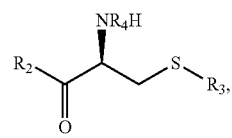

where $R_2$ is selected from the group consisting of: $NH_2$, $(C_{1-8}$ alkyl$)O-$, and OH.

In one embodiment, any one of $C_2$ through $C_7$ in the alkyl chain can be substituted with either nitrogen or oxygen.

In a preferred embodiment $R_2$ is t-butyl-O— or $(CH_3)(CH_2)O-$, $R_3$ is selected from the group consisting of:

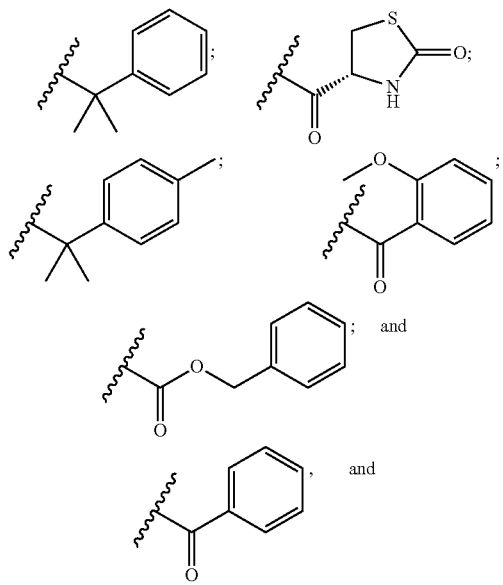

$R_4$ is selected from the group consisting of: H and

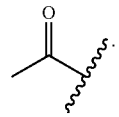

In particular, the invention provides the following compounds:

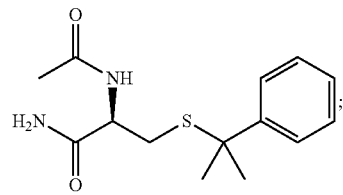

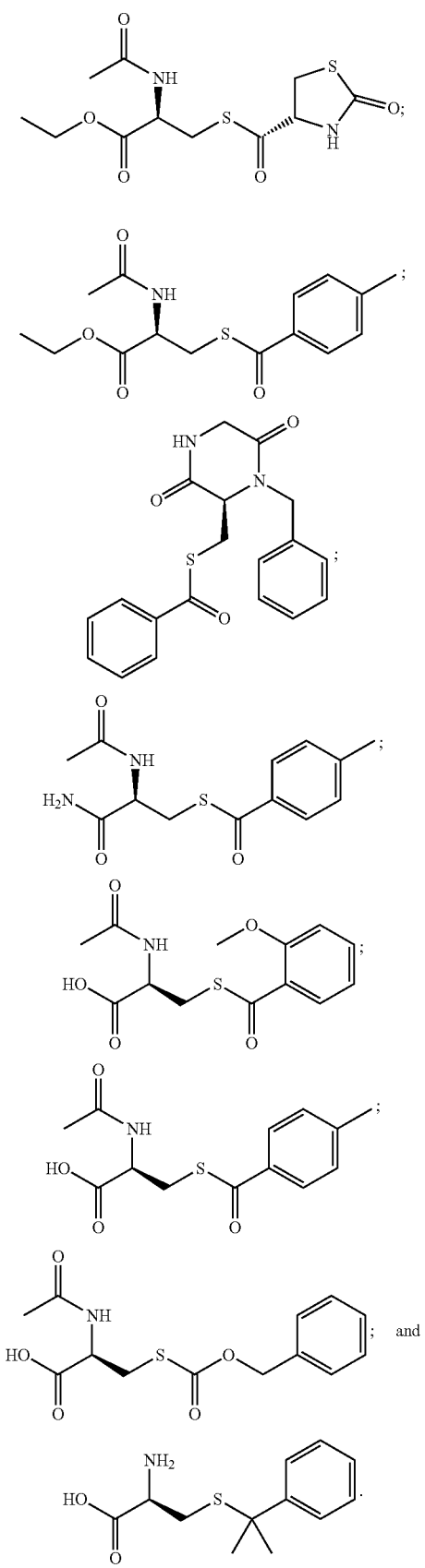

In another aspect, the present invention is directed to compounds of formula II:

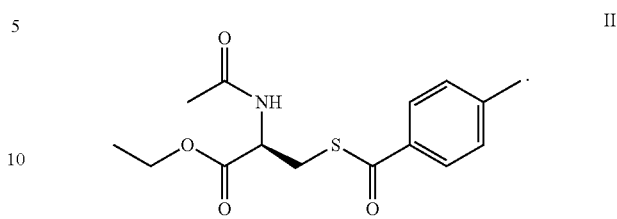

The invention also encompasses pharmaceutically acceptable salts, esters or prodrugs of the provided compounds.

Certain compounds of the invention may exist in different isomeric (e.g. enantiomers and distereoisomers) forms. The invention contemplates all such isomers both in pure form and in admixture, including racemic mixtures. Enol forms are also included.

The compounds of the invention can exist in unsolvated as well as solvated forms, including hydrated forms, e.g., hemi-hydrate. In general, the solvated forms, with pharmaceutically acceptable solvents such as water, ethanol, and the like are equivalent to the unsolvated forms for the purposes of the invention.

Certain compounds of the invention also form pharmaceutically acceptable salts, e.g., acid addition salts. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in J. Pharmaceutical Sciences, 66: 1 et seq. (1977). For example, for acid addition salts the nitrogen atoms may form salts with acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous hydroxide potassium carbonate, ammonia, and sodium bicarbonate. The free base forms differ from their respective salt forms somewhat in certain physical properties, such as solubility in polar solvents, but the acid salts are equivalent to their respective free base forms for purposes of the invention. (See, for example S. M. Berge, et al., "Pharmaceutical Salts," J. Pharm. Sci., 66: 1-19 (1977) which is incorporated herein by reference.)

As used herein, the term "composition" is intended to encompass a product comprising the specified ingredients in the specified amounts, as well as any product which results, directly or indirectly, from a combination of the specified ingredients in the specified amounts.

The compounds of the present invention can be used in the form of pharmaceutically acceptable salts derived from inorganic or organic acids. The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and quaternary ammonia and amine cations including ammonium, tetramethylammonium, tetraethylammonium, methylammonium, dimethylammonium, trimethylammonium, triethylammonium, diethylammonium, and ethylammonium among others. Other representative organic amines useful for the formation of base addition salts include ethylenediamine, ethanolamine, diethanolamine, piperidine, piperazine and the like.

Dosage forms for topical administration of a compound of this invention include powders, sprays, ointments and inhalants. The active compound is mixed under sterile conditions with a pharmaceutically acceptable carrier and any needed preservatives, buffers or propellants which can be required. Ophthalmic formulations, eye ointments, powders and solutions are also contemplated as being within the scope of this invention.

Actual dosage levels of active ingredients in the pharmaceutical compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the present invention can be employed in pure form or, where such forms exist, in pharmaceutically acceptable salt, ester or prodrug form. Alternatively, the compound can be administered as a pharmaceutical composition containing the compound of interest in combination with one or more pharmaceutically acceptable excipients.

The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.0001 to about 2000 mg/kg/day. For purposes of oral administration, more preferable doses can be in the range of from about 0.001 to about 15 mg/kg/day, with the most preferable dose being in the range of from about 0.001 to about 5 mg/kg/day. If desired, the effective daily dose can be divided into multiple doses for purposes of administration; consequently, single dose compositions may contain such amounts or submultiples thereof to make up the daily dose.

The present invention also provides pharmaceutical compositions that comprise compounds of the present invention formulated together with one or more pharmaceutically acceptable carriers. The pharmaceutical compositions can be specially formulated for oral administration in solid or liquid form, for parenteral administration or for rectal administration.

The pharmaceutical compositions of this invention can be administered to humans and other mammals orally, rectally, parenterally, intracisternally, intravaginally, transdermally (e.g. using a patch), transmucosally, sublingually, pulmonary, intraperitoneally, topically (as by powders, ointments or drops), bucally or as an oral or nasal spray. The terms "parental" or "parenterally," as used herein, refers to modes of administration which include intravenous, intramuscular, intraperitoneal, intrasternal, subcutaneous and intraarticular injection and infusion.

In another aspect, the present invention provides a pharmaceutical composition comprising a component of the present invention and a physiologically tolerable diluent. The present invention includes one or more compounds as described above formulated into compositions together with one or more physiologically tolerable or acceptable diluents, carriers, adjuvants or vehicles that are collectively referred to herein as diluents, for parenteral injection, for intranasal delivery, for oral administration in solid or liquid form, for rectal or topical administration, among others.

Compositions suitable for parenteral injection may comprise physiologically acceptable, sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), vegetable oils (such as olive oil), injectable organic esters such as ethyl oleate, and suitable mixtures thereof.

These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol, glycerol monostearate, and PEG caprylic/capric glycerides; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., *Methods in Cell Biology*, Volume XIV, Academic Press, New York, N.Y. (1976), p. 33 et seq.

In another aspect, the invention is directed to a method of treating a disease or condition in a subject comprising administering to the subject a therapeutically effective amount of a compound of any of Formulas I-II or a pharmaceutically acceptable salt, ester, or prodrug thereof. The preferred route of administering to the subject is via oral delivery.

Preferably, diseases or conditions treatable with the compounds of the present invention are related to the CNS. In a preferred embodiment, the disease is schizophrenia.

However, it is within a skill in the art that the provided compounds may be used to treat other diseases or conditions associated with diminished glutathione levels and/or glutamate signaling, and/or oxidative stress, and/or impaired cystine-glutamate antiporter activity, glutamate neurotransmission, synaptic connection, and gene expression.

In general, the invention is not limited to treatment of any specific disease or condition but encompasses the treatment of any disease or condition whose mechanism may be affected by the compounds of the present invention.

In another aspect, the invention provides a method of treating drug craving in a subject comprising administering to the subject a therapeutically effective amount of a compound of any of Formulas I-II or a pharmaceutically acceptable salt, ester or prodrug thereof. The preferred route of administering to the subject is via oral delivery.

The invention further encompasses pharmaceutical compositions containing a compound of any of Formulas I-II or a pharmaceutically acceptable salt, ester or prodrug thereof in combination with a pharmaceutically-acceptable carrier.

Methods of formulating/manufacturing such pharmaceutical compositions (alternatively termed "medicaments") for the treatment of a disease or condition in a subject are also within the invention's scope.

For a clearer understanding of the invention, Examples are provided below. These are merely illustrations and are not to be understood as limiting the scope of the invention in any way. Indeed, various modifications of the invention in addition to those shown and described herein will become apparent to those skilled in the art from the following examples and foregoing description. Such modifications are also intended to fall within the scope of the appended claims.

EXAMPLES

Example 1—Synthesis Strategies

General Methods

All solvents used were commercially available and were used without further purification. Reactions were typically run using anhydrous solvents under an inert atmosphere of nitrogen. Compounds are named using ChemDraw 7, Reaxys or catalogue names if commercially available.

$^1$H and $^{13}$C NMR spectra were recorded at 400 MHz for proton and 100 MHz for carbon-13 on a Varian 300 MercuryPlus station with an Oxford AS400 Spectrometer equipped with a Varian 400 ATB PFG probe. All deuterated solvents contained typically 0.03% to 0.05% v/v tetramethylsilane, which was used as the reference signal (set at $\delta$ 0.00 for $^1$H and $^{13}$C). For $^{13}$C, the shifts were relative to the DMSO-d6 assignment of $\delta\delta$ 39.50.

Mass spectra were recorded on a Waters MS consisting of an Alliance 2795 (LC) and Waters Micromass ZQ detector at 120° C. The mass spectrometer was equipped with an electrospray ion source (ES) operated in a positive or negative mode. The mass spectrometer was scanned between m/z 100-1000 with a scan time of 0.3 s.

Elemental Analysis for C, H and N composition was performed using a Costech Instrument Elemental Combustion System ECS4010 with a helium flow of 100 mL/min (14 psi), oxygen 20 mL/min (10 psi), air 25 psi and purge of 50 mL/min (N42) or at the University of Alberta Analytical and Instrumentation Laboratory (N39).

Ultra-performance liquid chromatography (UPLC) analyses were performed on a Water 600 Controller system with a Waters 717 Plus Autosampler and a Waters 2996 Photodiode Array Detector. The column used was an Atlantis T3 d18 4.6×150 mm 3 μm and a gradient was applied, starting at 100% A (A: 0.1% $H_3PO_4$ in water) and ending at 30% (B: MeCN) over 10 min and then increased to 95% B where it was maintained for 2 min. The column was then re-equilibrated to 100% A for the remainder of the 20 min. The column temperature was at ambient temperature with the flow rate of 0.9-1.2 mL/min. The Diode Array Detector was scanned from 200-400 nm.

Thin layer chromatography ("TLC") was performed on Alugram® (silica gel 60 $F_{254}$; Alugram is a registered trademark of Macherey, Nagel & Co.) and ultra violet light ("UV") was typically used to visualize the spots. Additional visualization methods were also employed in some cases. For example, the TLC plate could also be developed with iodine (generated by adding approximately 1 g of $I_2$ to 10 g silica gel and thoroughly mixing), vanillin (generated by dissolving about 1 g vanillin in 100 mL 10% $H_2SO_4$), ninhydrin (available commercially from Aldrich), or Magic Stain (generated by thoroughly mixing 25 g $(NH_4)_6Mo_7O_{24}.4H_2O$, 5 g $(NH_4)_2Ce(IV)(NO_3)_6$ in 450 mL water and 50 mL concentrated $H_2SO_4$) to visualize the compound. Medium pressure chromatography was performed with a Biotage SP4® (Biotage is a registered trademark of Biotage AB) using SNAP™ silica gel cartridges or Teledyne Isco cartridges. Flash chromatography was preformed using typically 40-63 μm (230-400 mesh) silica gel from Silicycle following analogous techniques to those disclosed in Still et al. (Still, W. C.; Kahn, M.; and Mitra, M., *Journal of Organic Chemistry*, 43: 2923-2925 (1978)). Typical solvents used for Biotage®, flash chromatography or thin layer chromatography were mixtures of chloroform/methanol, dichloromethane/methanol, ethyl acetate/methanol and hexanes/ethyl acetate.

Optical rotation was performed on a Perkin Elmer 241 Polarimeter at the University of Alberta, Edmonton, Alberta Analytical and Instrumentation Lab with a 10.002 cm path length.

Melting points were determined on an Electrothermal Digital Melting Point Apparatus (S.No 2345, Cat. No. IA8101) and are uncorrected.

The following abbreviations have been used:
aq. aqueous;
DMSO dimethylsulfoxide;
EtOAc ethyl acetate;
HOAc acetic acid;
MeOH methanol;
NMM 4-methylmorpholine;
ON overnight;
r.t. room temperature;
TFA trifluoroacetic acid; and
THF tetrahydrofuran.

Starting materials used were available from commercial sources and used as received.

Synthesis of N42: (2R)-2-Acetylamino-3-[(4R)-2-oxo-thiazolidine-4-carbonylsulfanyl]-propionic acid

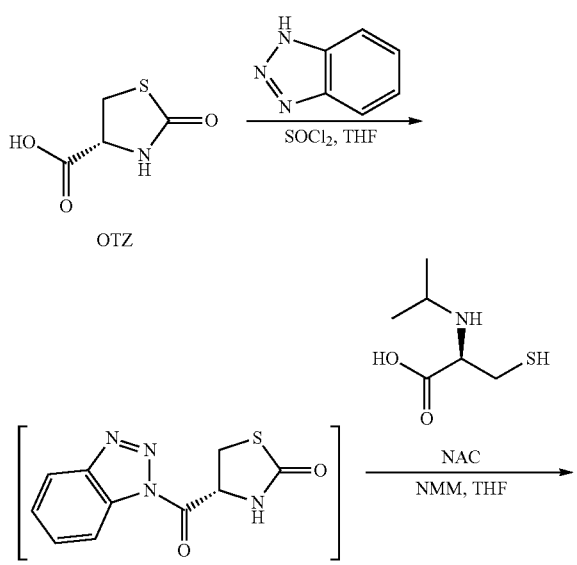

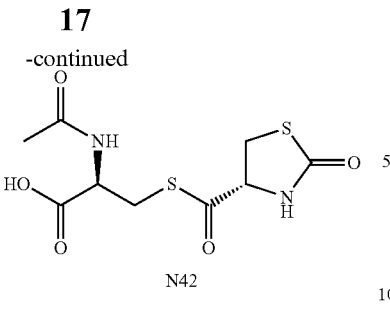

N42

The following procedure was performed based on the thioester formation conditions reported in Katritzky, A. R.; Tala, S. R.; Abo-Dya, N. E.; Ibrahim, T. S.; El-Feky, S. A.; Gyanda, K.; Pandya, K. M., *J. Org. Chem.*, 76: 85-96 (2011).

(2R)-2-Acetylamino-3-[(4R)-2-oxo-thiazolidine-4-carbonylsulfanyl]-propionic acid (N42, Ref. 10-015-161)

To a solution of 1H-benzotriazole (19.4 g, 163 mmol) in THF (180 mL) was added thionyl chloride (2.96 mL, 40.8 mmol). The solution was cooled in an icebath and after 0.5 h, (4R)-2-oxo-thiazolidine-4-carboxylic acid (OTZ, 6.00 g, 40.8 mmol) was added. The solution warmed slowly to ambient temperature over 1 h. After 1.25 h at room temperature, the resulting solid was removed by vacuum filtration. With 60 mL THF to wash the solid and flask, the filtrate was transferred to an ice cold solution of (2R)-2-acetylamino-3-mercapto-propionic acid (NAC, 6.00 g, 36.7 mmol) and NMM (4.04 mL, 36.7 mmol) in THF (30 mL). The ice bath was removed. After 30 min, the reaction appeared complete by $^1$HNMR. To the mixture was added TFA and the resulting solution was split in two and applied to two 330 g silica gel Isco columns pre-wet with ethyl acetate. Biotage chromatography of the two columns (EtOAc to 20% methanol (0.5% AcOH)) generated 2.36 g (97.35% HPLC purity) of the title compound after EtOAc trituration and drying in vacuo. Addition compound was obtained by concentration the fast running UV active fractions and triturating with EtOAc. The solid was then dissolved in water, filtered and lyophilized generating the title compound as a white lyophilizate. This material was combined with a batch from the EtOAc mother liquor and was absorbed to 25 g silica gel with ~1:1 EtOAc-MeOH. Biotage purification (330 g Isco, EtOAc to 20% methanol (0.5% AcOH), pre-wet column with EtOAc) generated 0.84 g (light yellow lyophilizate, 94.70% HPLC purity) and 3.74 g (white lyophilizate, 96.88% HPLC purity) after dissolving in water, filtering and lyophilizing. Yield: 6.94 g (65%).

$^1$H NMR (400 MHz, DMSO-$d_6$) δ 13.01 (br.s, 1H), 8.95 (d, J=2.0 Hz, 1H), 8.33 (d, J=8.2 Hz, 1H), 4.61-4.57 (m, 1H), 4.39-4.33 (m, 1H), 3.81 (dd, J=11.7, 9.0 Hz, 1H), 3.43 (dd, J=11.7, 2.3 Hz, 1H), 3.39 (dd, J=13.3, 4.7 Hz, 1H), 3.08 (dd, J=13.7, 8.6 Hz, 1H), 1.84 (s, 3H); $^{13}$C NMR (100.6 MHz, DMSO-$d_6$) 200.9, 173.5, 171.6, 169.4, 61.7, 51.2, 32.7, 30.0, 22.3 ppm; MS (ES) m/z: 293 (M+H)$^+$; HPLC: 96.88% (MaxPlot 220-400 nm); Elemental analysis for $C_9H_{12}N_2O_5S_2$: Calcd: C, 36.98%; H, 4.14%; N, 9.58%. Found: C, 36.80%; H, 4.24%; N, 9.63%. $[α]_D^{25}$ −71.58 (c 1.0, water).

Synthesis of N50: (2R)-2-Acetylamino-3-(2-methoxy-benzoylsulfanyl)-propionic acid

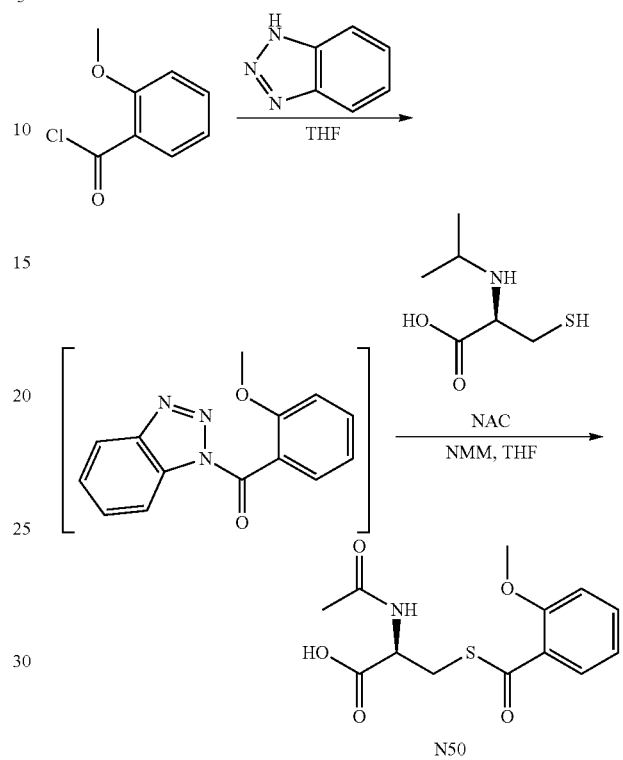

The following procedure was performed based on the thioester formation conditions reported in Katritzky, A. R.; Tala, S. R.; Abo-Dya, N. E.; Ibrahim, T. S.; El-Feky, S. A.; Gyanda, K.; Pandya, K. M., *J. Org. Chem.*, 76: 85-96 (2011).

(2R)-2-Acetylamino-3-(2-methoxy-benzoylsulfanyl)-propionic acid (N50, Ref. 10-015-179-7)

To a solution of 1H-benzotriazole (7.68 g, 64.4 mmol) in THF (60 mL) was added 2-methoxy-benzoyl chloride (4.36 mL, 29.3 mmol). After 15 min the resulting solution turned cloudy and the mixture was stirred for 1.75 h longer. The resulting solid was removed by vacuum filtration with 15 mL THF wash. The resulting filtrate, with 15 mL THF wash, was added to pre-cooled solution of (2R)-2-acetylamino-3-mercapto-propionic acid (NAC, 3.83 g, 23.4 mmol) and NMM (2.57 mL, 23.4 mmol) in THF (30 mL). The ice bath was removed. After overnight a room temperature the reaction was not complete by $^1$HNMR. More NMM (2.57 mL, 23.4 mmol) was added and the mixture was heated to 55° C. overnight. To the mixture was added TFA (4 mL) and the solution was concentrated in vacuo. The residue was dissolved in MeOH and EtOAc and was absorbed to ~80 g silica gel. Purification was accomplished by Biotage silica gel chromatography (330 g ISCO column, 120 mL 1:2 EtOAc-hexanes then 120 mL 1:1 then EtOAc to 20% MeOH (1% AcOH) gradient) followed by precipitation by dissolving in a warm MeCN/water 1:1 mixture (100 mL), removing the MeCN in vacuo, and collecting the precipitate by suction filtration, with water wash, after standing overnight at ambient temperature. The title compound was isolated as a white solid. Yield: 2.29 g (33%).

Mp 179-181° C. $^1$H NMR (399.7 MHz, DMSO-d$_6$) δ 12.89 (br.s, 1H), 8.31 (d, J=8.2 Hz, 1H), 7.65 (dd, J=7.8, 1.6 Hz, 1H), 7.59-7.54 (m, 1H), 7.18 (d, J=8.6 Hz, 1H), 7.06-7.02 (m, 1H), 4.42-4.36 (m, 1H), 3.85 (s, 3H), 3.47 (dd, J=13.7, 5.1 Hz, 1H), 3.11 (dd, J=13.7, 9.0 Hz, 1H), 1.82 (s, 3H); $^{13}$C NMR (100.5 MHz, DMSO-d$_6$) 189.4, 171.8, 169.3, 157.4, 134.3, 129.0, 125.9, 120.4, 113.8, 55.9, 51.4, 30.3, 22.3 ppm; MS (ES) m/z: 298 (M+H)$^+$; HPLC: 97.72% (MaxPlot 220-400 nm); Elemental analysis for C$_{13}$H$_{15}$NO$_5$S: Calcd: C, 52.51%; H, 5.09%; N, 4.71%; S, 10.78%. Found: C, 52.58%; H, 5.07%; N, 4.82%; S, 10.55%. [α]D$^{25}$ −21.49 (c 1.014, DMSO).

Synthesis of N51: (2R)-2-Acetylamino-3-(4-methyl-benzoylsulfanyl)-propionic acid (Pro-2023)

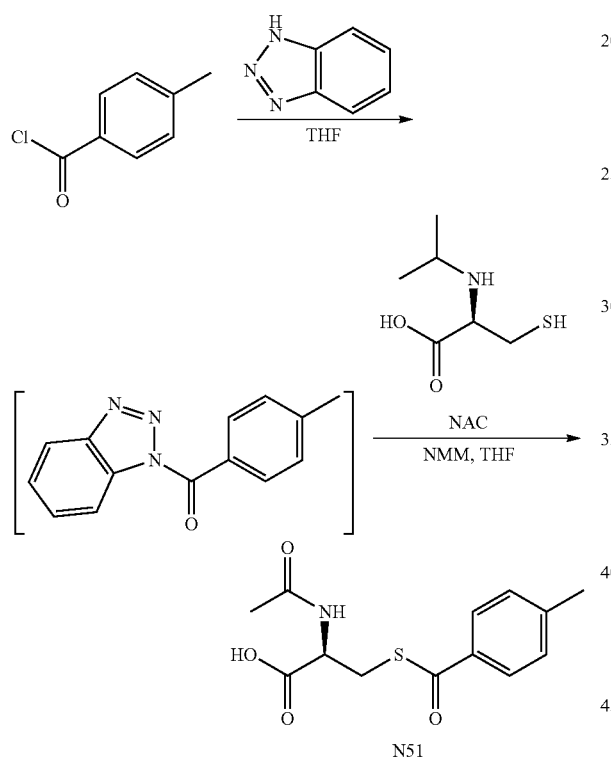

The following procedure was performed based on the thioester formation conditions reported in Katritzky, A. R.; Tala, S. R.; Abo-Dya, N. E.; Ibrahim, T. S.; El-Feky, S. A.; Gyanda, K.; Pandya, K. M., *J. Org. Chem.*, 76: 85-96 (2011).

(2R)-2-Acetylamino-3-(4-methyl-benzoylsulfanyl)-propionic acid (N51, Ref. 10-015-177-7)

To a solution of 1H-benzotriazole (9.91 g, 83.2 mmol) in THF (80 mL) was added 4-methyl-benzoyl chloride (5.00 mL, 37.8 mmol). After 2 h, the resulting solid was removed by vacuum filtration with 25 mL THF wash. The resulting filtrate, with 25 mL THF wash, was added to pre-cooled solution of (2R)-2-acetylamino-3-mercapto-propionic acid (NAC, 5.55 g, 34.0 mmol) and NMM (3.74 mL, 34.0 mmol) in THF (50 mL). The ice bath was removed. After overnight a room temperature the reaction was not complete by $^1$HNMR. The mixture was heated to 55° C. for 1 h. To the mixture was added TFA (3.6 mL) and water (100 mL). The solution was concentrated in vacuo to remove most of the THF. More water (80 mL) and dichloromethane (180 mL) were added and the layers separated. The aqueous layer was extracted with dichloromethane. The organic layers were combined, dried over Na$_2$SO$_4$, filtered, ethyl acetate added (100 mL) and concentrated in vacuo to remove dichloromethane. The remaining ethyl acetate solution was place briefly in the freezer to start crystallization then left out overnight at ambient temperature. The solid obtained was collected by vacuum filtration generating 3.28 g after drying and the filtrate, with some methanol added, was absorbed to 85 g silica gel. Biotage column chromatography (330 g ISCO, hexanes-ethyl acetate 1:1 (0.5 CV) then EtOAc to 20% MeOH (1% AcOH) gradient) yielded 2.62 g of material. The solid from EtOAc precipitation and the material off the column were combined and dissolved in warm MeCN/water 1:1 mixture. The MeCN was removed in vacuo, and the precipitate that formed after leaving at ambient temperature overnight was collected by suction filtration. The title compound was isolated as a white solid. Yield: 4.81 g (50%).

Mp 182-184° C. $^1$H NMR (399.7 MHz, DMSO-d$_6$) □ 12.98 (br.s, 1H), 8.38 (d, J=7.8 Hz, 1H), 7.82 (d, J=8.0 Hz, 2H), 7.37 (d, J=8.0 Hz, 2H), 4.47-4.42 (m, 1H), 3.55 (dd, J=13.7, 5.1 Hz, 1H), 3.23 (dd, J=13.7, 8.6 Hz, 1H), 2.89 (s, 3H), 1.84 (s, 3H); $^{13}$C NMR (100.5 MHz, DMSO-d$_6$) 189.9, 171.7, 169.3, 144.6, 133.6, 129.6, 127.0, 51.4, 29.9, 22.3, 21.2 ppm; MS (ES) m/z: 282 (M+H)$^+$; HPLC: 94.77% (MaxPlot 220-400 nm); Elemental analysis for C$_{13}$H$_{15}$NO$_4$S: Calcd: C, 55.50%; H, 5.37%; N, 4.98%; S, 11.40%. Found: C, 55.46%; H, 5.33%; N, 5.08%; S, 11.66%. [α]D$^{25}$ −23.74 (c 1.0, DMSO).

Synthesis of N53: (2R)-2-Acetylamino-3-benzyloxycarbonylsulfanyl-propionic acid

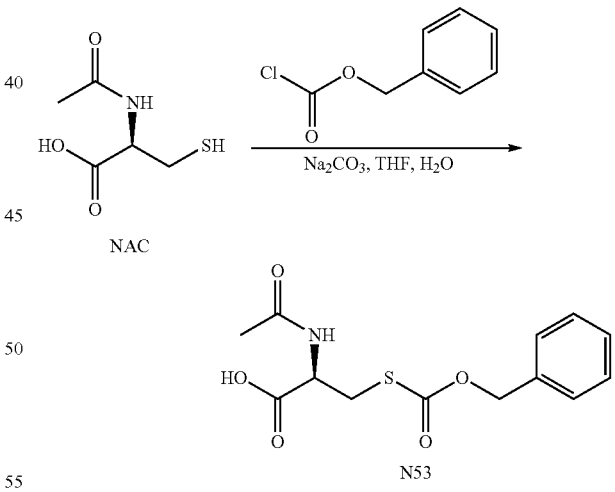

The following procedure was performed based on the thiocarbonate formation conditions reported in Crankshaw, D. L.; Berkely, L. I.; Cohen, J. F.; Shirota, F. N.; Nagasawa, H. T., *Journal of Biochemical and Molecular Toxicology*, 16: 235-244 (2002).

(2R)-2-Acetylamino-3-benzyloxycarbonylsulfanyl-propionic acid (N53, Ref. 10-015-183-7)

To a solution of 2R)-2-acetylamino-3-mercapto-propionic acid (NAC, 4.02 g, 24.6 mmol) in water (30 mL) was added sodium carbonate (2.64 g, 24.9 mmol) followed by THF (30 mL). Then benzyl chloroformate (7.73 mL, 54.1 mmol) was added. After 1 h, more sodium carbonate was added to adjust pH to ~8. After additional 0.5 h, partially concentrate in vacuo. Extract aqueous with EtOAc (3×) then acidify aqueous with 2 N HCl to pH~3. Add ether and separate layers. Extract aqueous with EtOAc (2×) and combine organic layers, dry over Na$_2$SO$_4$, filter and concentrate in vacuo. Purification was accomplished by Biotage column chromatography (330 g ISCO, 1:1 hex/EtOAc (120 mL) then EtOAc to 20% MeOH (1% AcOH) gradient, sample loaded in EtOAc with some hexanes) generated the title compound as a white solid. Yield: 2.18 g (30%).

Mp 146-148° C. $^1$H NMR (399.7 MHz, DMSO-d$_6$) δ 12.98 (br.s, 1H), 8.33 (d, J=8.2 Hz, 1H), 7.40-7.32 (m, 5H), 5.27-5.20 (m, 2H), 4.44-4.38 (m, 1H), 3.35-3.30 (dd, partially masked by H$_2$O, 1H), 3.05 (dd, J=14.0, 8.6 Hz, 1H), 1.81 (s, 3H); $^{13}$C NMR (100.5 MHz, DMSO-d$_6$) 171.6, 169.6, 169.4, 135.2, 128.5$_4$, 128.4$_7$, 128.3$_8$, 68.9, 51.5, 32.1, 22.3 ppm; MS (ES) m/z: 298 (M+H)$^+$; HPLC: 98.22% (MaxPlot 220-400 nm); Elemental analysis for C$_{13}$H$_{15}$NO$_5$S: Calcd: C, 52.51%; H, 5.09%; N, 4.71%; S, 10.78%. Found: C, pending %; H, pending %; N, pending %; S, pending %. [α]D$^{25}$ pending (c,).

Specific Methods $^1$H-NMR spectra were obtained on a Varian Mercury 300-MHz NMR. Purity (%) was determined with a Waters Alliance 2695 HPLC (Waters Symmetry C18, 4.6×75 mm, 3.5 µm) with a 2996 diode array detector from 210-400 nm.

Synthesis of Ethyl (2R)-2-acetamido-3-(4-methyl-benzoylsulfanyl)propanoate (Pro-4051)

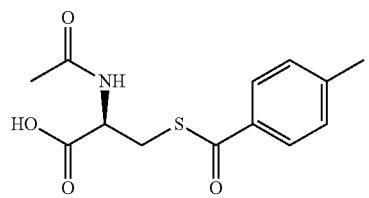 [SMILES: CC(=O)N[C@@H](CSC(=O)c1ccc(C)cc1)C(=O)O]

2-Acetylamino-3-(4-methyl-benzoylsulfanyl)-propionic acid

To a solution of benzotriazole (9.91 g, 83.2 mmol) in tetrahydrofuran (80 mL) was added 4-methylbenzoyl chloride (5.0 mL, 37.8 mmol) (5 g, 95%). After 2 hours, the resulting slurry was filtered and the solid was rinsed with tetrahydrofuran (25 mL). The filtrates were combined and added to a solution of N-acetyl-L-cysteine (5.55 g, 34.0 mmol) and N-methylmorpholine (3.74 mL, 34.0 mmol) in tetrahydrofuran (50 mL) at 0° C. The resulting mixture was allowed to warm to ambient temperature over 16 hours. Aqueous hydrochloric acid (1 M, 100 mL) was added to the mixture and the resulting mixture was concentrated at reduced pressure to a volume of approximately 125 mL. Additional aqueous hydrochloric acid (80 mL) was added and the mixture was extracted with dichloromethane (180 mL then 80 mL). The combined organic extracts were combined, dried over sodium sulfate, filtered and concentrated at reduced pressure. Ethyl acetate (100 mL) was added and the resulting slurry was stirred for 2 hours. The resulting slurry was filtered and dried to give a white solid (5.7 g, 60%). $^1$H NMR (300 MHz, DMSO) δ=12.94 (s, 1H), 8.34 (d, J=7.9 Hz, 1H), 7.86-7.74 (m, 2H), 7.35 (d, J=8.5 Hz, 2H), 4.43 (dt, J=5.0, 8.4 Hz, 1H), 3.53 (dd, J=5.0, 13.8 Hz, 1H), 3.21 (dd, J=8.5, 13.8 Hz, 1H), 2.37 (s, 3H), 1.83 (s, 3H). MS (ESI) m/z 282 (M+1)$^+$.

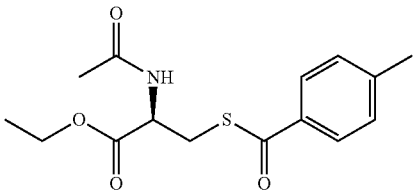 [SMILES: CCOC(=O)[C@H](CSC(=O)c1ccc(C)cc1)NC(C)=O]

Ethyl (2R)-2-acetamido-3-(4-methylbenzoylsulfanyl)propanoate

To a solution of 2-acetylamino-3-(4-methyl-benzoylsulfanyl)-propionic acid (1.1 g, 3.91 mmol) and triethylamine (0.68 mL, 4.89 mmol) N,N-dimethylformamide (5 mL) was added iodoethane (0.39 mL, 4.89 mmol) and the resulting solution was stirred at ambient temperature for 18 hours. The reaction mixture was added slowly to water (50 mL) with rapid stirring. After stirring for 2 hours, the resulting slurry was filtered and the solid was rinsed with water and dried under vacuum to give the product as a white solid (780 mg, 60%). $^1$H NMR (300 MHz, DMSO) δ=8.47 (d, J=7.9 Hz, 1H), 7.81 (s, 1H), 7.80-7.78 (m, 1H), 7.35 (d, J=7.6 Hz, 2H), 4.46 (dt, J=5.3, 8.1 Hz, 1H), 4.09 (q, J=6.8 Hz, 2H), 3.50 (dd, J=5.4, 13.6 Hz, 1H), 3.24 (dd, J=8.2, 13.8 Hz, 1H), 2.37 (s, 3H), 1.83 (s, 3H), 1.16 (t, J=7.0 Hz, 3H). MS (ESI) m/z 310 (M+1)$^+$.

Synthesis of (2R)-2-acetamido-3-(4-methylbenzoylsulfanyl)propanamide (Pro-4051A)

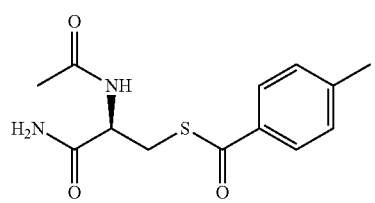 [SMILES: CC(=O)N[C@@H](CSC(=O)c1ccc(C)cc1)C(N)=O]

To a solution of 2-acetylamino-3-(4-methyl-benzoylsulfanyl)-propionic acid (500 mg, 1.78 mmol), N-(3-dimethylaminopropyl)-N'-ethylcarbodiimide hydrochloride (686 mg, 3.58 mmol), hydroxybenzotriazole hydrate (483 mg, 3.58 mmol) and triethylamine (0.50 mL, 3.58 mmol) in N,N-dimethylformamide (5 mL) was added ammonium chloride (191 mg, 3.58 mmol) and the resulting slurry was stirred at ambient temperature for 18 hours after which time a solution formed. The mixture was diluted with ethyl acetate (100 mL) and wash successively with hydrochloric acid (0.1 M, 50 mL), saturated aqueous sodium hydrogen carbonate (50 mL). the organic layer was dried over magnesium sulfate, filtered and concentrated at reduced pressure to give an oil. This crude product was purified with silica gel (12 g) chromatography eluting with 50 to 100% ethyl acetate in hexane. The purified fractions were combined and concentrated at reduced pressure to give the product as a white solid (55 mg, 11%). $^1$H NMR (300 MHz, DMSO) δ=8.16 (d, J=8.5 Hz, 1H), 7.79 (d, J=8.2 Hz, 2H), 7.47 (br. s., 1H), 7.35 (d, J=8.2 Hz, 2H), 7.19 (br. s., 1H), 4.43 (dt, J=5.4, 8.3 Hz, 1H), 3.42 (dd, J=5.4, 13.3 Hz, 1H), 3.16 (dd, J=8.4, 13.3 Hz, 1H), 2.32 (s, 3H), 1.85 (s, 3H). MS (ESI) m/z 281 (M+1)⁺.

Synthesis of (2R)-2-Acetamido-3-[(2-phenylpropan-2-yl)sulfanyl]propanamide (Pro-4006)

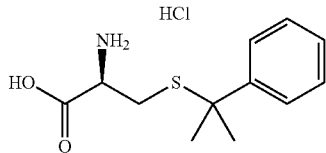 [SMILES: Cl ; CC(C)(SC[C@H](N)C(=O)O)c1ccccc1]

(2R)-2-Amino-3-(1-methyl-1-phenyl-ethylsulfanyl)-propionic acid hydrochloride

To a solution of L-cysteine hydrochloride (2 g, 12.7 mmol) in aqueous hydrochloric acid (2M, 30 mL) was added 2-phenyl-propan-2-ol (1.78 mL, 12.7 mmol) and the resulting mixture was heated in an oil bath at 65-75° C. for 18 hours. The reaction mixture was cooled and filtered and rinsed with aqueous hydrochloric acid (1M, 10 mL) to give a white solid (2.2 g, 63%). ¹H NMR (300 MHz, DMSO) δ=8.62 (br. s, 3H), 7.55-7.43 (m, 2H), 7.37-7.19 (m, 3H), 7.23-7.17 (m, 1H), 3.80 (m, 1H), 2.70-2.64 (m, 2H), 1.64 (s, 6H).

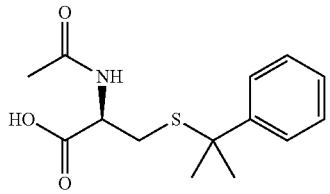 [SMILES: CC(=O)N[C@@H](CSC(C)(C)c1ccccc1)C(=O)O]

(2R)-2-Acetylamino-3-(1-methyl-1-phenyl-ethylsulfanyl)-propionic acid

To a mixture of (2R)-2-amino-3-(1-methyl-1-phenyl-ethylsulfanyl)-propionic acid hydrochloride (1.0 g, 3.63 mmol) in water (5 mL) and 1,4-dioxane (5 mL) at 0° C. was added aqueous sodium hydroxide (2M) to pH 10, then acetic anhydride (0.34 mL, 3.63 mmol) was added dropwise. The reaction mixture was warmed to ambient temperature over 16 hours. The reaction mixture was acidified to pH 2 with aqueous hydrochloric acid (1 M) and extracted with ethyl acetate (60 mL×2). The combined organic layers were dried over magnesium sulfate, filtered and concentrated at reduced pressure to give the crude product which was used in the next step without further purification.

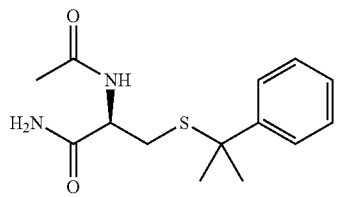 [SMILES: CC(=O)N[C@@H](CSC(C)(C)c1ccccc1)C(N)=O]

(2R)-2-Acetamido-3-[(2-phenylpropan-2-yl)sulfanyl]propanamide

To a solution of (2R)-2-acetylamino-3-(1-methyl-1-phenyl-ethylsulfanyl)-propionic acid (400 mg, 1.42 mmol), N-(3-dimethylaminopropyl)-N'-ethylcarbodiimide hydrochloride (545 mg, 2.84 mmol), hydroxybenzotriazole hydrate (384 mg, 2.84 mmol) and triethylamine (0.40 mL, 2.84 mmol) in N,N-dimethylformamide (2 mL) was added ammonium chloride (152 mg, 2.84 mmol) and the resulting slurry was stirred at ambient temperature for 18 hours after which time a solution formed. The mixture was diluted with ethyl acetate (100 mL) and wash successively with hydrochloric acid (0.1 M, 50 mL), saturated aqueous sodium hydrogen carbonate (50 mL). The organic layer was dried over magnesium sulfate, filtered and concentrated at reduced pressure to give an oil. This crude product was purified with silica gel (12 g) chromatography eluting with 50 to 100% ethyl acetate in hexane. The purified fractions were combined and concentrated at reduced pressure to give the product as a white solid (145 mg, 36%). ¹H NMR (300 MHz, DMSO) δ=7.92 (d, J=8.2 Hz, 1H), 7.52-7.46 (m, 2H), 7.37-7.28 (m, 3H), 7.23-7.17 (m, 1H), 7.04 (s, 1H), 4.21 (dt, J=6.0, 8.1 Hz, 1H), 2.47-2.32 (m, 2H), 1.79 (s, 3H), 1.62 (d, J=4.1 Hz, 6H). MS (ESI) m/z 281 (M+1)⁺.

Synthesis of Ethyl (2R)-2-acetamido-3-(2-oxo-1,3-thiazolidine-4-carbonylsulfanyl) propanoate (Pro-4047)

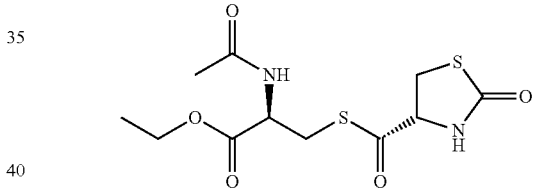

To a solution of L-2-oxothiazolidine-4-carboxylic acid (6.0 g, 40.8 mmol), N-(3-dimethylaminopropyl)-N'-ethylcarbodiimide hydrochloride (9.03 g, 47.1 mmol) and hydroxybenzotriazole hydrate (6.4 g, 47.1 mmol) in N,N-dimethylformamide (30 mL) was added 2-acetylamino-3-mercapto-propionic acid ethyl ester (6.0 g, 31.4 mmol) and the resulting slurry was stirred at ambient temperature for 72 hours during which time a solution formed. The mixture was diluted with aqueous hydrochloric acid (0.2 M, 300 mL) and extracted with ethyl acetate (4×200 mL). The combined organic layers were washed with saturated aqueous sodium hydrogen carbonate (150 mL). The organic layer was dried over magnesium sulfate, filtered and concentrated at reduced pressure. This crude product was purified with silica gel (120 g) chromatography eluting with 30 to 100% ethyl acetate in hexane. The purified fractions were combined and concentrated at reduced pressure. The resulting solid was triturated with ethyl acetate/hexanes (1:1, 100 mL), filtered and dried to give the product as a white solid (3.1 g, 31%). ¹H NMR (300 MHz, CDCl₃) δ=6.33-6.20 (m, 2H), 4.87 (ddd, 5.9, 7.5 Hz, 1H), 4.43 (ddd, J=1.8, 3.5, 8.5 Hz, 1H), 4.22 (dq, J=2.3, 7.1 Hz, 2H), 3.79 (dd, J=8.5, 11.4 Hz, 1H), 3.62-3.51 (m, 2H), 3.40-3.31 (m, 1H), 2.05-2.02 (m, 3H), 1.60 (s, 2H), 1.31 (t, J=7.2 Hz, 3H). MS (ESI) m/z 321 (M+1)⁺.

Synthesis of (6R)-1-benzyl-6-(sulfanylmethyl)piperazine-2,5-dione

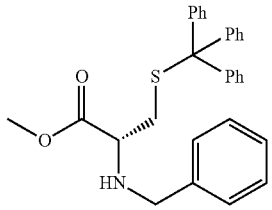 [SMILES: COC(=O)[C@H](CSC(c1ccccc1)(c1ccccc1)c1ccccc1)NCc1ccccc1]

(2R)-2-Benzylamino-3-tritylsulfanyl-propionic acid methyl ester

To a solution of (2R)-2-Amino-3-tritylsulfanyl-propionic acid methyl ester (41 g, 109 mmol) in methanol (570 mL) was added benzaldehyde (13.3 mL, 131 mmol). After 1.5 hours, the reaction mixture was cooled in an ice bath and sodium borohydride (8.25 g, 218 mmol) was added in portions over 20 minutes. One addition was complete, the ice bath was removed and the reaction was allowed to warm to ambient temperature over one hour. The resulting mixture was then concentrated under reduced pressure. The resulting oil was diluted with water (300 mL) and ethyl acetate (500 mL) and the layers were separated. The organic layer was washed again with water (200 mL) and the organic layer was dried over magnesium sulfate, filtered and concentrated at reduced pressure. The crude product was purified with silica gel (330 g) chromatography eluting with 0 to 20% ethyl acetate in hexane. The purified fractions were combined and concentrated at reduced pressure to give the product as a colorless oil (30.5 g, 60%). $^1$H NMR (300 MHz, CDCl$_3$) δ=7.44-7.37 (m, 6H), 7.31-7.17 (m, 14H), 3.69-3.62 (m, 4H), 3.60-3.51 (m, 1H), 3.14-3.07 (m, 1H), 2.50 (d, J=6.4 Hz, 2H).

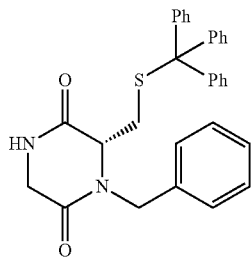 [SMILES: O=C1NCC(=O)N(Cc2ccccc2)[C@H]1CSC(c1ccccc1)(c1ccccc1)c1ccccc1]

(6R)-1-benzyl-6-{[(triphenylmethyl)sulfanyl]methyl}piperazine-2,5-dione

To a solution of (2R)-2-benzylamino-3-tritylsulfanyl-propionic acid methyl ester (30.2 g, 64.6 mmol) and diisopropylethylamine (12.4 mL, 71 mmol) in dichloromethane (400 mL) at 0° C. was added bromoacetyl bromide (6.2 mL, 71 mmol) in dichloromethane (30 mL) dropwise via an addition funnel. The reaction mixture was allowed to warm to ambient temperature over 2 hours. The reaction was diluted with dichloromethane (300 mL) and extracted with aqueous hydrochloric acid (0.5 N, 400 mL). The aqueous layer was extracted with dichloromethane (100 mL) and the combined organic extracts were dried over magnesium sulfate, filtered and concentrated at reduced pressure. To this crude product was added a solution of ammonia in methanol (7 M, 200 mL) and the resulting solution was stirred at ambient temperature over 64 hours. The reaction mixture was concentrated at reduced pressure. The resulting mixture was triturated vigorously with aqueous hydrochloric acid (200 mL) for 3 hours and filtered. The solid was dissolved in dichloromethane and purified with silica gel (330 g) chromatography eluting with 0 to 70% ethyl acetate in hexane. The purified fractions were combined and concentrated at reduced pressure to give the product as a white solid (14.1 g, 44% over two steps). $^1$H NMR (300 MHz, CDCl$_3$) δ=7.42-7.37 (m, 6H), 7.33-7.21 (m, 12H), 7.02 (dd, J=2.8, 6.6 Hz, 2H), 6.64 (d, J=2.6 Hz, 1H), 5.26 (d, J=15.0 Hz, 1H), 4.27 (d, J=17.3 Hz, 1H), 3.98-3.83 (m, 2H), 3.20 (d, J=15.0 Hz, 1H), 2.94 (dd, J=3.7, 12.5 Hz, 1H), 2.55 (dd, J=5.0, 12.6 Hz, 1H). MS (ESI) m/z 493 (M+1)$^+$.

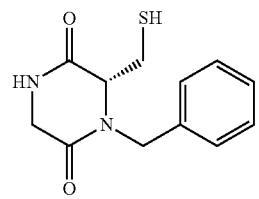 [SMILES: O=C1NCC(=O)N(Cc2ccccc2)[C@H]1CS]

(6R)-1-benzyl-6-(sulfanylmethyl)piperazine-2,5-dione

To a solution of (6R)-1-benzyl-6-{[(triphenylmethyl)sulfanyl]methyl}piperazine-2,5-dione (13 g, 26.4 mmol) in trifluoroacetic acid (100 mL) and dichloromethane (200 mL) at 0° C. was added triisopropylsilane (21.6 mL, 106 mmol) dropwise. After addition was complete, the reaction mixture was allowed to warm to ambient temperature over 2 hours. Heptane (100 mL) was added and the mixture was concentrated at reduced pressure. The crude product was purified with silica gel (120 g) chromatography eluting with 0 to 100% ethyl acetate in hexane. The purified fractions were combined and concentrated at reduced pressure. The solid was triturated with ethyl acetate (50 mL) to give the product as an off-white solid (6.0 g, 90%). $^1$H NMR (300 MHz, CDCl$_3$) δ=7.38-7.26 (m, 5H), 6.63 (br. s., 1H), 5.20 (d, J=15.0 Hz, 1H), 4.43 (d, J=17.3 Hz, 1H), 4.16-4.05 (m, 3H), 4.01 (d, J=2.9 Hz, 1H), 3.12 (ddd, J=2.3, 10.2, 14.7 Hz, 1H), 2.96 (ddd, J=4.1, 8.4, 14.8 Hz, 1H), 1.65 (s, 1H), 1.41 (dd, J=8.4, 10.1 Hz, 1H). MS (ESI) m/z 251 (M+1)$^-$.

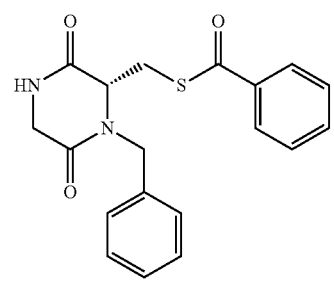 [SMILES: O=C(SC[C@H]1C(=O)NCC(=O)N1Cc1ccccc1)c1ccccc1]

Synthesis of (6R)-6-[(benzoylsulfanyl)methyl]-1-benzylpiperazine-2,5-dione (Pro-4011)

To a stirring solution of (6R)-1-benzyl-6-(sulfanylmethyl)piperazine-2,5-dione (200 mg, 0.79 mmol) in pyridine (3 mL) at 0° C. was added benzoyl chloride (0.23 mL, 1.98 mmol) dropwise and when addition was complete, the reaction mixture was warmed to ambient temperature and stirred for 24 hours. The reaction was concentrated at reduced pressure, diluted with dichloromethane (100 mL) was washed with saturated aqueous sodium hydrogen carbonate (30 mL) then aqueous hydrochloric acid (0.1N, 40 mL). The organic layer was dried over magnesium sulfate, filtered and concentrated at reduced pressure. The crude product was purified with silica gel (20 g) chromatography eluting with 20 to 100% ethyl acetate in hexane. The purified fractions were combined and concentrated at reduced pressure. The solid was triturated with ethyl acetate/hexanes (1:1, 10 mL) to give the product as a white solid (77 mg, 27%). $^1$H NMR (300 MHz, DMSO) δ=8.37 (d, J=3.5 Hz, 1H), 7.92 (d, J=7.8 Hz, 2H), 7.74-7.67 (m, 1H), 7.60-7.53 (m, 2H), 7.37-7.24 (m, 5H), 5.06 (d, J=15.0 Hz, 1H), 4.21-4.10 (m, 2H), 4.04 (dd, 5.7 Hz, 1H), 3.81-3.71 (m, 2H), 3.55 (dd, J=3.8, 14.1 Hz, 1H), 3.40-3.34 (m, 1H), 3.32-3.25 (m, 1H). MS (ESI) m/z 355 (M+1)$^+$.

Example 2—In Vitro Studies $^{14}$C Uptake by Compounds of the Invention

The goal of these experiments was to determine $^{14}$C-cystine uptake.

The experiments were conducted as follows.

The screening of compounds was performed using an in vitro culture system of human glial cells from brain astrocytoma (1321N1). Cells were plated on 24 well plates coated with poly-D-lysine and laminin and grown in a balanced salt solution supplemented with 5% heat inactivated horse serum, 5% fetal bovine serum, 2 mM glutamine and glucose (total 21 mM). Cultures were maintained in humidified 5% $CO_2$ incubators at 37° C. for 3-4 days before experiments were performed, at this time the cultures has formed a single confluent layer. For experiments, cultures were washed 3 times into a Na-free HEPES and $HCO_3^-$ buffered balanced salt solution. After 1 hour, the test compounds are added. Following a three hour incubation, $^{14}$C-cystine (0.025 mCi/mL) was then added for 20 minutes. Following the $^{14}$C-cystine exposure, cultures were washed 3 times with ice cold HEPES buffered saline solution and dissolved in 250 µl sodium dodecyl sulfate (0.1%). An aliquot (200 µl) was removed and added to scintillation fluid for counting. Values were normalized to $^{14}$C-cystine uptake in untreated controls on the same experimental plate.

$^3$H-Glutamate Release by Compounds of the Invention

This assay also uses the cell culture system of human glial cells from brain astrocytoma (1321N1) described above. Initially, cells are washed with HBBSS, and $^3$H-glutamate is added (PerkinElmer: 1 mCi/mL stock solution is diluted (30 µL+500 µL HBBSS) and 10 µL of diluted radiolabel is added to each well). Following a 1 hour incubation to load the cells with the labeled glutamate, the cells are washed again with HBBSS, and the drug is added. At 30, 90, and 180 minutes, 50 µL of extracellular media is sampled from each well and is measured using a Beckman LS 6500 scintillation counter.

Results of the $^{14}$C-cystine uptake and $^3$H-glutamate release by astrocytes treated with differing concentrations of Pro-2022, Pro-2023, Pro-4006, Pro-4011, Pro-4047, Pro-4051 and Pro-4051a, are presented in FIGS. 1, 2 and 5-9, respectively, as a percentage of the untreated control. Only $^{14}$C-cystine uptake data was obtained for Pro-2024 and Pro-3010. The most effective concentration of Pro 2022 for radiolabeled cystine uptake was 300 µM which surprisingly shows an increase of about 50% over the untreated control. This data suggest interaction with the target (System xc-) albeit in an unexpected manner. The most effective concentration of Pro-2022 for glutamate release was 100 µM at 3 hours incubation which produced an approximately 60% increase. The most effective concentration of Pro-2023 for radiolabeled cystine uptake was 1000 µM which produced an approximately 45% decrease in $^{14}$C-cystine uptake demonstrating inhibition of $^{14}$C-cystine uptake by a process not limited to an alternate substrate, a cystine-glutamate antiporter inhibitor, and an effective prodrug. The most effective concentration of Pro-2023 for glutamate release was 300 µM which produced an approximately 135% increase at 3 hours, which is evidence that the $^{14}$C-cystine uptake is being inhibited by direct competition from Pro-2023. The most effective concentration of Pro-2024 for radiolabeled cystine uptake was 100 µM which surprisingly showed an increase. 300 and 1000 µM concentrations produced inhibition of radiolabeled cystine uptake of approximately 30% and 35%, respectively. The most effective concentration of Pro-3010 was 1000 µM which produced an approximately 75% decrease in radiolabeled cystine uptake. The most effective concentration of Pro-4006 was 30 µM which produced an approximately 45% decrease in $^{14}$C-cystine uptake with a corresponding 35% increase in $^3$H-glutamate release at 30 minutes. Based on previous solubility studies with related analogues, it is postulated that the 1000 µM dose is likely out of solution; nonetheless, we have included this high concentration of Pro-4006 in the current data set. The most effective concentration of Pro-4011 was 100 µM which surprisingly produced an approximately 75% increase in $^{14}$C-cystine uptake with a corresponding 75% increase in $^3$H-glutamate release at 3 hours. The 300 and 1000 µM data points may be aberrant due to the appearance of precipitates in the assay media suggesting the compound was not in solution. Pro-4047 produced an approximate 20-60% decrease in $^{14}$C-cystine uptake demonstrating a dose-dependent decrease. The most effective concentration of Pro 4047 for glutamate release was 100 µM which produced an approximately 40% increase at 3 hours. The most effective concentration of Pro-4051 was 100 µM which produced an approximately 28% decrease in $^{14}$C-cystine uptake. This graph represents an average of three experiments run. Pro-4051 is not in solution above 316 µM according to solubility data. The most effective concentration of Pro-4051 for $^3$H-glutamate release was 300 µM which produced an approximately 100% increase at 3 hours. Pro-4051a did not produce a substantial inhibition of $^{14}$C-cystine uptake. This is likely because the 3 hour incubation does not fall within the window of efficacy for this compound. The most effective concentration of Pro-4051a for $^3$H-glutamate release was 1000 µM which produced an approximately 180% increase at 30 minutes.

In Vitro Thiol Experiments

To further resolve by what process the inhibition of $^{14}$C-cystine uptake is occurring intracellular cysteine levels were determined.

The experiment was conducted as follows.

Mixed cortical cell cultures containing glial and neuronal cells were prepared from fetal (15-16 day gestation) mice as previously described. (Lobner D, "Comparison of the LDH and MTT assays for quantifying cell death: validity for neuronal apoptosis?," *J. Neurosci. Methods,* 96(2): 147-152 (Mar. 15, 2000)). Dissociated cortical cells were plated on 24-well plates coated with poly-D-lysine and laminin in Eagles' Minimal Essential Medium (MEM, Earle's salts, supplied glutamine-free) supplemented with 5% heat-inactivated horse serum, 5% fetal bovine serum, 2 mM glutamine and glucose (total 21 mM). Cultures were maintained in humidified 5% $CO_2$ incubators at 37° C. Mice were handled in accordance with a protocol approved by our institutional animal care committee and in compliance with the Public Health service Policy on Humane Care and Use of Laboratory Animals.

Mixed cortical cell cultures, 14 days in vitro (this allows for a confluent layer of astrocytes to form and the neurons to generate a complex network of axons and dendrites), were washed into bicarbonate buffered salt solution. After 1 hour, 3, 10, 30, 100 μM of Pro-4047 or Pro-4051 was added and the cells were incubated for 30 or 90 minutes, after which the cells were thoroughly washed and the collected in 250 μL of aqueous mobile phase (50 mM citric acid, 10 mM octanesulfonic acid, pH 2.8) was added, after 10 minutes at 37° C. the cells were scraped from the plates and transferred to 1.5 mL tubes for analysis.

Samples were then sonicated with a Fisher Scientific 60 Sonic Dismembrator. One fraction of this homogenate was analyzed with the Pierce BCA (bicinchoninic acid) method to determine protein concentration. The other fraction was filtered using 3 K molecular weight cutoff, polyethersulfone centrifugal protein filters, and analyzed for thiol content using HPLC (ALF-115 column, 150×1.0 mm, 3 μm C18 [Pro-2023 analysis utilized a Phenomenex Kinetex 2.6 μM, C18, 100A, 150×2.1 mm and Pro-4047 analysis utilized a Phenomenex Kinetex X-B, C18, 100 A, 2.6 μm, 150×4.4 mm]; mobile phase: 50 mM citric acid, 10 mM octanesulfonic acid, 2% acetonitrile, pH 2.8, 50 μL/min flow rate [Pro-2023 analysis utilized a 100 μL/min flow rate and Pro-4047 analysis utilized 1% acetonitrile and 0.4 mL/min flow rate] with electrochemical detection (Decade II, Au working electrode, Flex Cell HyREF, 0.55V, Antec Leyden, Netherlands [Pro-4047 analysis utilized a Magic Diamond working electrode and 1.8V]).

Figure 10:
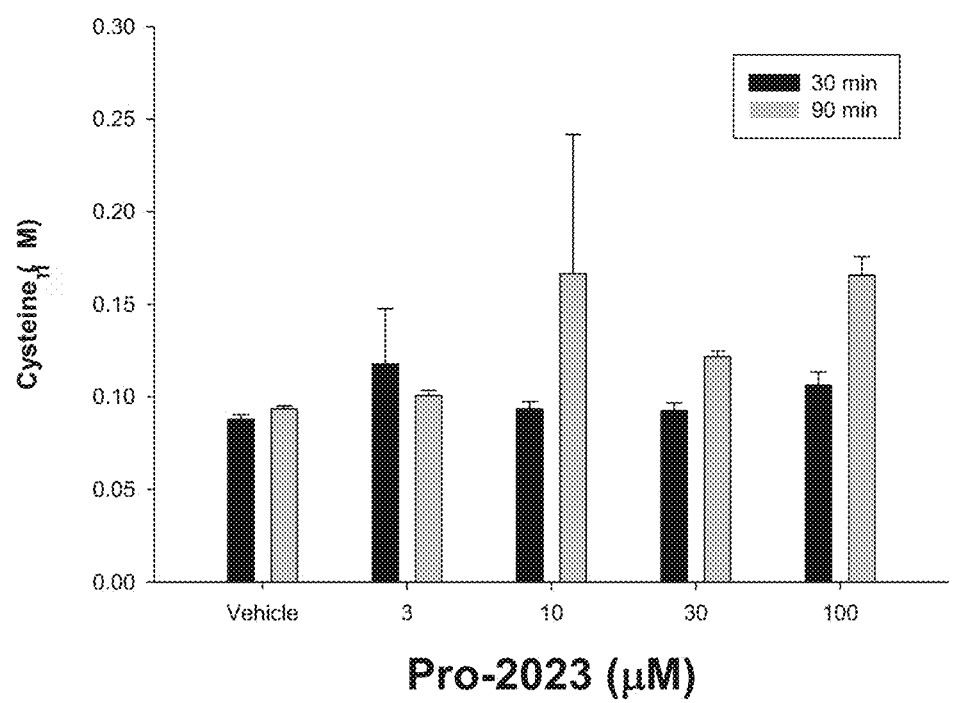
FIG. 10 is a graphical representation of the amount of intracellular cysteine for Pro-2023.
Figure 11:
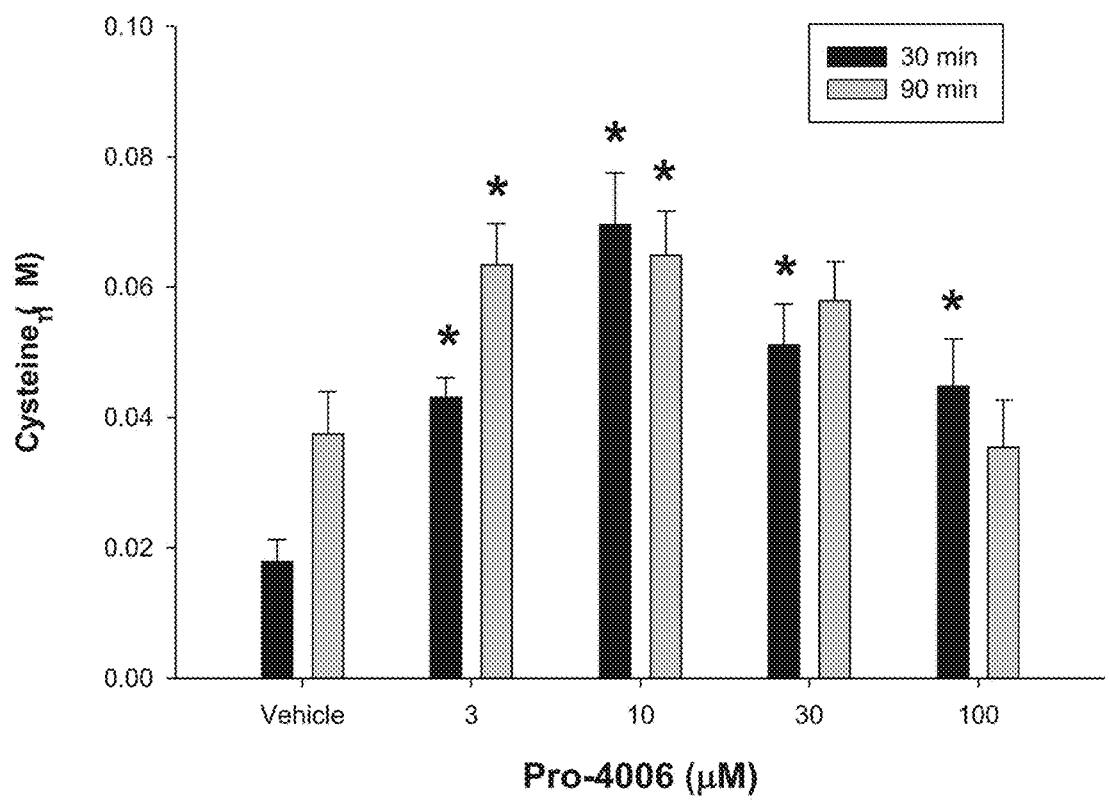
FIG. 11 is a graphical representation of the amount of intracellular cysteine for Pro-4006.
Figure 12:
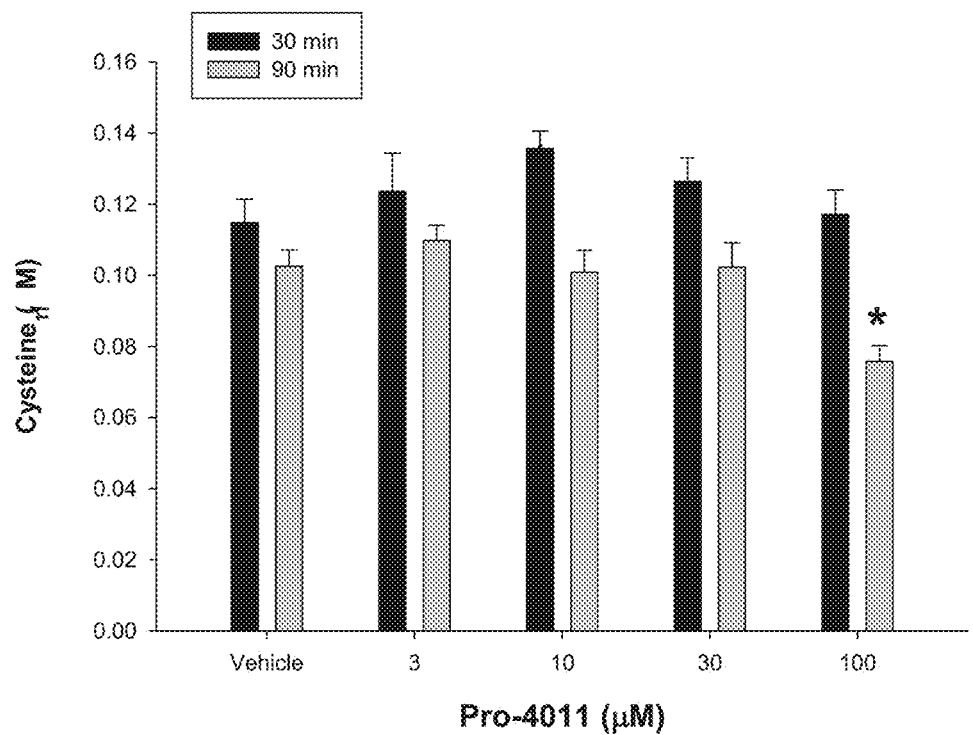
FIG. 12 is a graphical representation of the amount of intracellular cysteine for Pro-4011.
Figure 13:
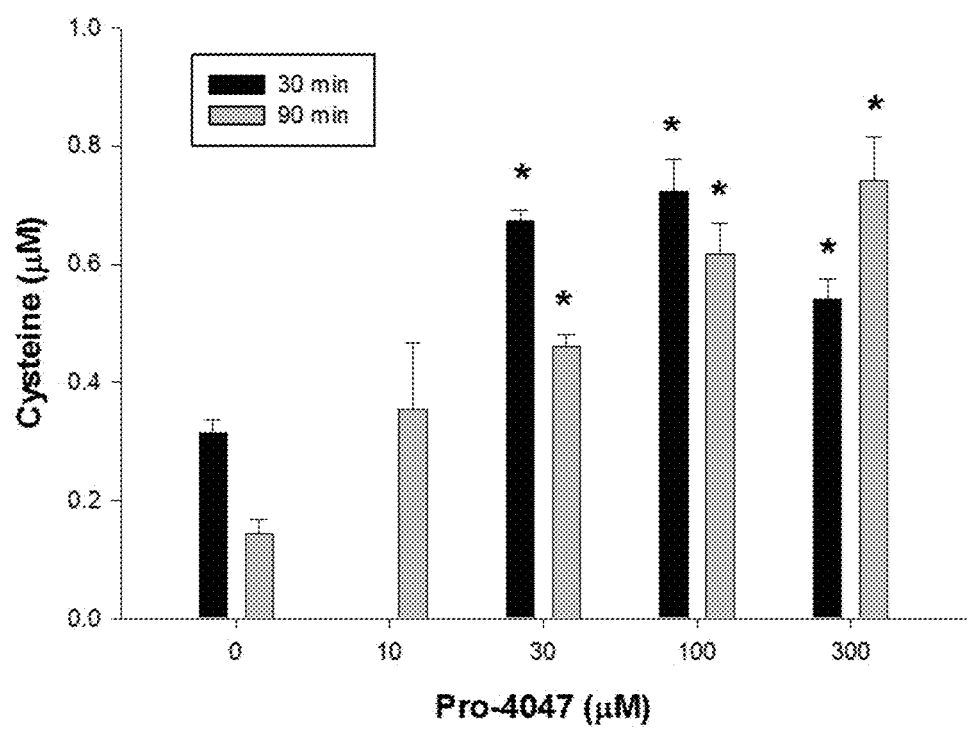
FIG. 13 is a graphical representation of the amount of intracellular cysteine for Pro-4047.
Figure 14:
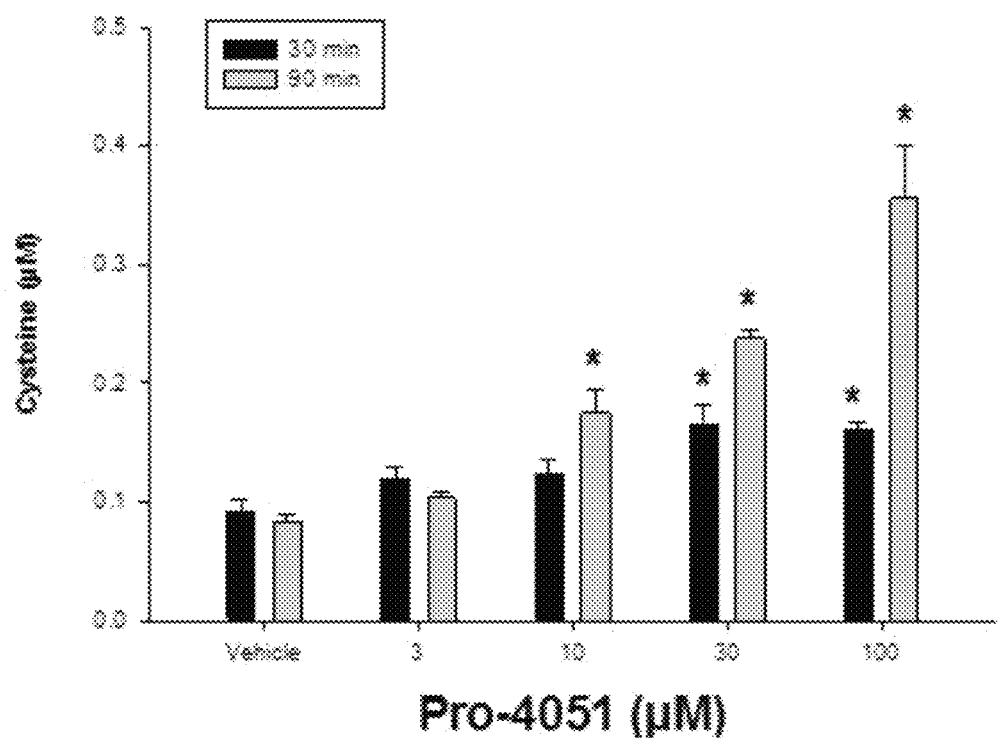
FIG. 14 is a graphical representation of the amount of intracellular cysteine for Pro-4051.
Figure 15:
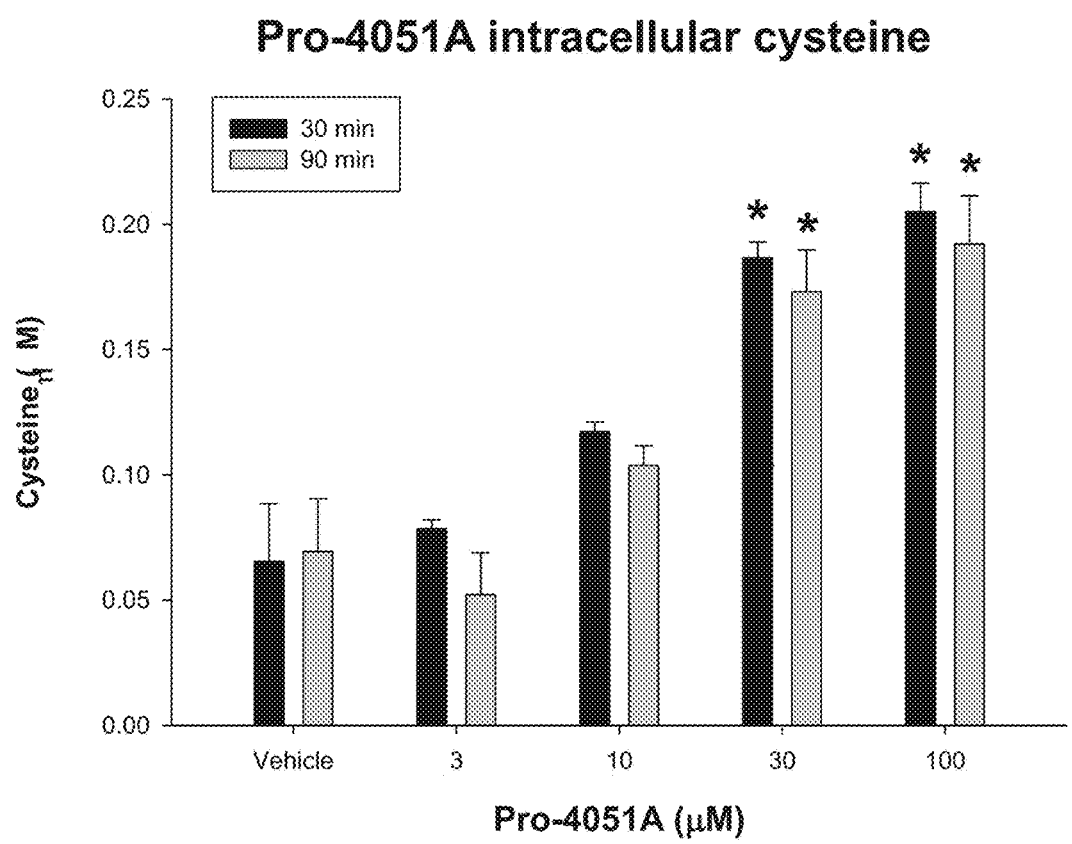

When the intracellular thiol assay was initiated, all data was normalized to protein concentration. However, the protein method did not produce consistent results in control samples, so that method of normalization was abandoned. The data presented herein represents the raw cysteine concentrations in the collected samples. Results demonstrate that administration of Pro-2023 at 100 μM increases intracellular cysteine concentration to 0.16 μM at 30 minutes (approximately 1.6 times that of the control; FIG. 10). Pro-4006 at 10 μM increases intracellular cysteine concentration to 0.07 μM at 30 minutes (approximately 3.5 times that of the control; FIG. 11). Pro-4011 at 10 μM increases intracellular cysteine concentration to 0.138 μM at 30 minutes (approximately 1.16 times that of the control; FIG. 12). Pro-4047 at 300 μM increases intracellular cysteine concentration to 0.74 μM at 90 minutes (approximately 4.9 times that of the control; FIG. 13). FIG. 14 demonstrates that administration of Pro-4051 at 100 μM increases intracellular cysteine concentration to 0.36 μM at 90 minutes (approximately 4 times that of the control). Finally, FIG. 15 demonstrates that administration of Pro-4051a at 100 μM increases intracellular cysteine concentration to 0.21 μM at 30 minutes (approximately 3 times that of the control). These results demonstrate that Pro-2023, Pro-4006, Pro-4011, Pro-4047, Pro-4051 and Pro-4051a were effectively cleaved, yielding an increase in intracellular cysteine. Thus, based on the 3 in vitro experiments it is apparent that Pro-2023, Pro-4006, Pro-4011, Pro-4047, Pro-4051 and Pro-4051a behave as effective cysteine prodrugs.

Example 3—In Vivo Studies

Prepulse Inhibition Experiment

The goal of this experiment was to demonstrate the efficacy of the test compounds in a predictive animal model of schizophrenia.

The experiment was conducted as follows.

Rats were placed on a platform in a sound attenuating chamber (10.875"×14"×19.5"; Hamilton Kinder, CA) that rested on a motion sensing plate. During all sessions, the background noise was held constant at 60 dB. A matching session was conducted to determine the magnitude of the average startle response for each rat. This session consisted of a five minute habituation period followed by 20 trials; 17 trials involved the presentation of a single auditory stimulus (pulse stimulus; 50 dB above the background noise) and three trials in which a pre-pulse stimulus (12 db above background) was presented 100 ms before the pulse auditory stimulus. Rats were then assigned into the various treatment groups so that the magnitude of the startle response was equivalent across all groups. Two days later, a testing session was conducted to assess sensorimotor gating. One hour prior to testing, rats received a prodrug (0-100 mg/kg, P.O.) and 55 minutes later acute MK-801 maleate (0.1 mg/kg, SC). The testing session consisted of a five minute habituation period, after which rats received 58 discrete trials; 26 trials during which the pulse stimulus (50 db above background) was presented alone, eight trials each in which the pulse stimulus was preceded by a prepulse stimulus (5, 10, or 15 db above background) and eight background trials with no pulse (No stimulus; background noise only). The first six pulse alone trials were not included in the average startle stimulus to achieve a relatively stable level of startle reactivity. All startle responses were normalized to vehicle control, and the percent of prepulse inhibition was determined as 100-(average prepulse startle response/average startle stimulus alone)*100.

Figure 16:
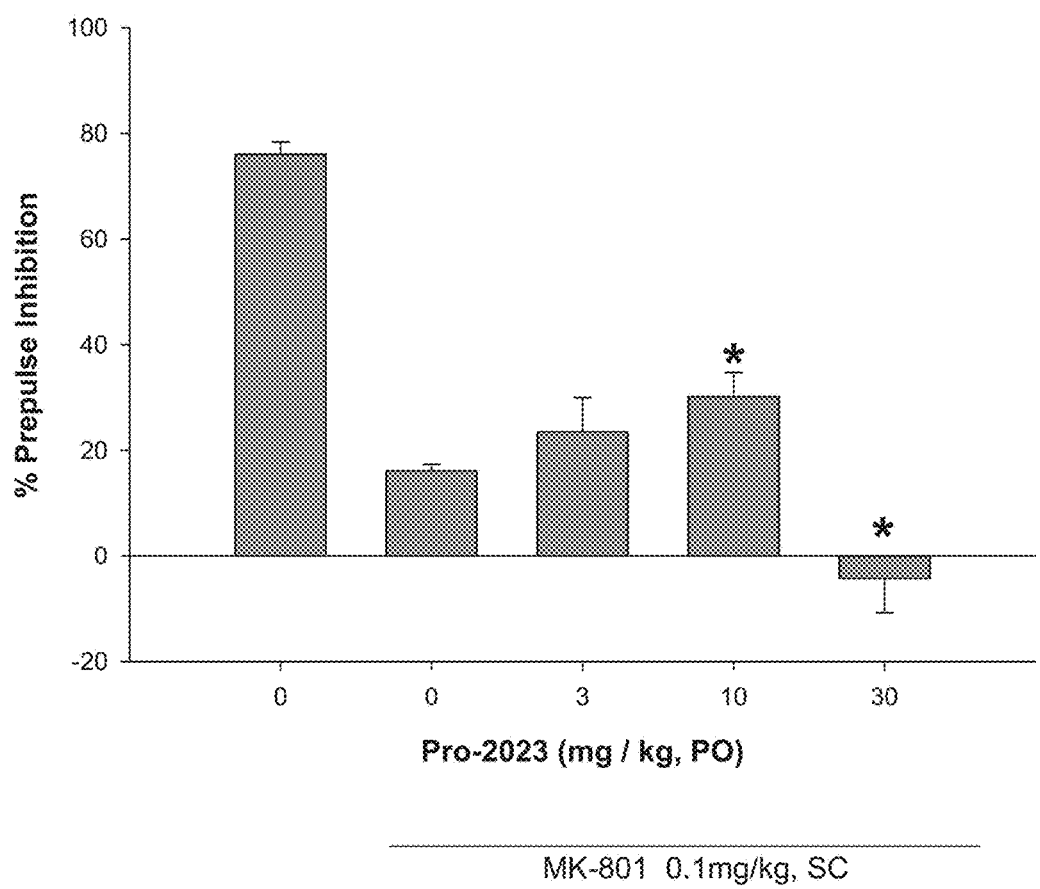
FIG. 16 is a graphical representation of prepulse inhibition for Pro-2023.

FIG. 16 depicts the average prepulse inhibition for Pro-2023. As the bar graph demonstrates, at 10 mg/kg concentration, % prepulse inhibition was about 30% as opposed to about 16% for the control group that received both MK-801 and vehicle. Consistent with similar dose-response curves in this assay (including clozapine), the compound produces an inverted U-shaped dose response at higher concentrations. These data, which are consistent to the effects of clinically-used neuroleptics, suggest antipsychotic-like activity in rodent model of schizophrenia.

Figure 17:
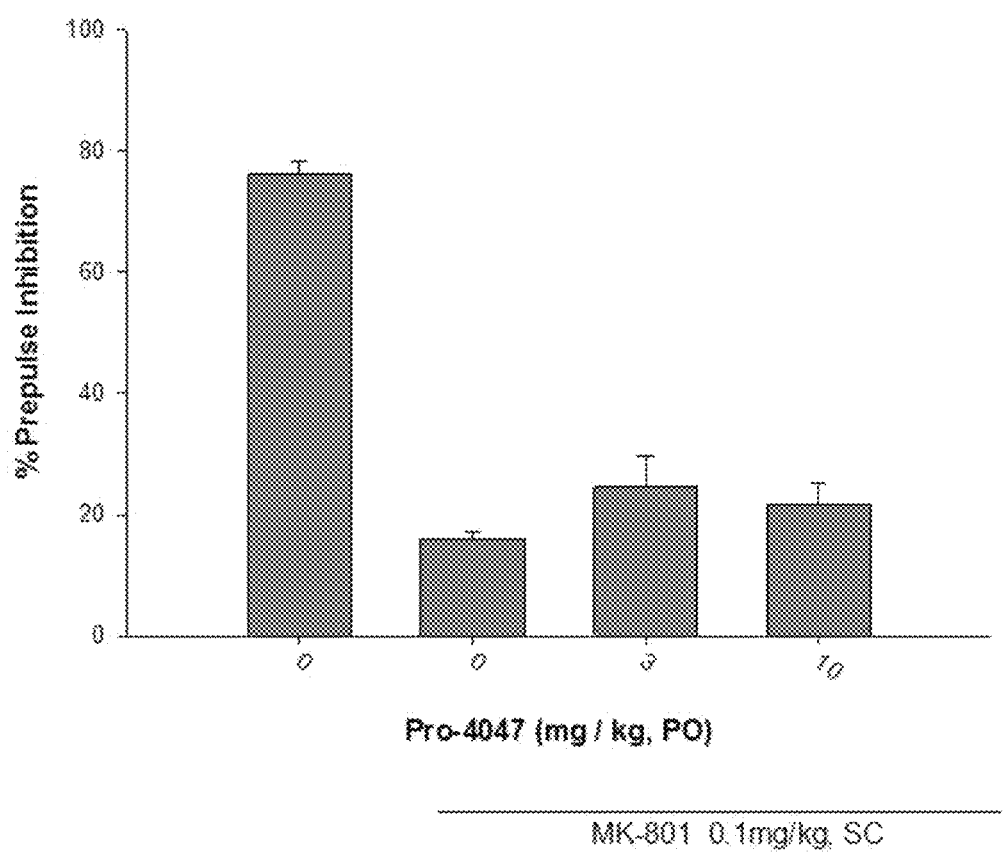
FIG. 17 is a graphical representation of prepulse inhibition for Pro-4047.

FIG. 17 depicts the average prepulse inhibition for Pro-4047. As the bar graph demonstrates, at 3 mg/kg concentration, % prepulse inhibition was about 23% as opposed to about 16% for the control group that received both MK-801 and vehicle. The general lack of efficacy in this model, despite activity in the primary cell-based assays, is likely due to either pharmacokinetic parameters that are such that the therapeutic window was missed with the single time-point tested. Additionally, this could be due to the dose-range tested where higher doses (e.g. 30 or 60 mg/kg) could have produced an effect.

Figure 18:
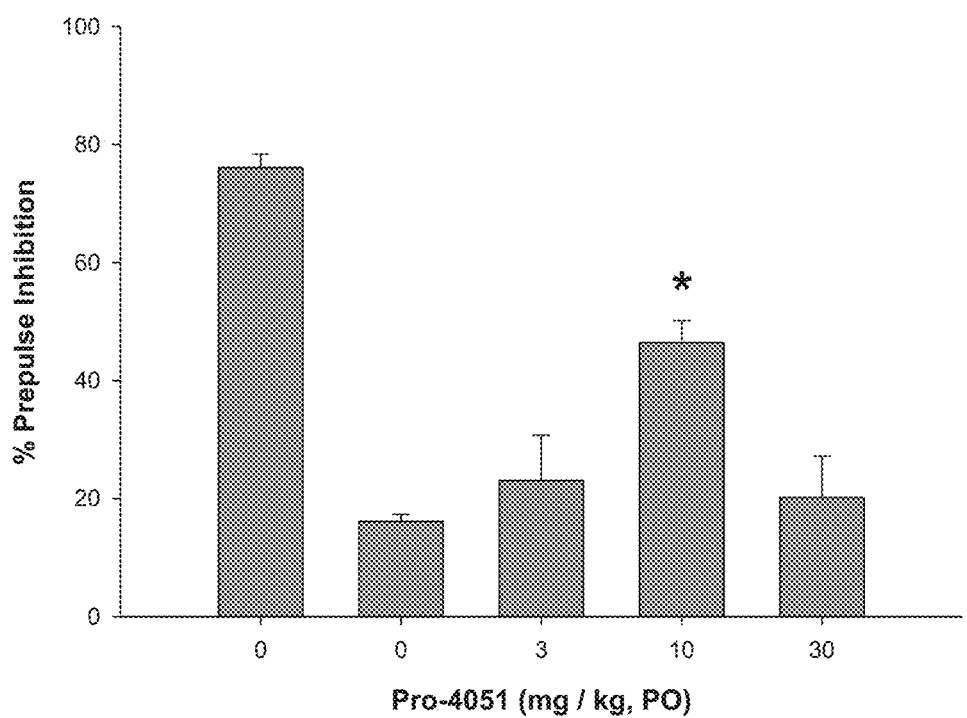
FIG. 18 is a graphical representation of prepulse inhibition for Pro-4051.

FIG. 18 demonstrate the results of the experiment for Pro-4051. As the bar demonstrates, at 10 mg/kg concentration, % prepulse inhibition was about 46%, as compared to about 16% for the control group that received both MK-801 and vehicle.

These results mean that this compound significantly ameliorates the schizophrenia-like MK-801-induced deficit in prepulse inhibition.

Elevated-Plus Maze

The goal of this experiment was to demonstrate the ability of the test compounds to penetrate the CNS.

The experiment was conducted as follows.

Rats were tested in a standard elevated plus maze; testing occurred in a dimly illuminated room using only two lights mounted over the maze. Animals were allowed to habituate to the room for at least one hour prior to treatment. One hour prior to testing, rats received a compound of the present invention (0-30 mg/kg, P.O.). For testing, the rat was placed in the elevated plus maze for five minutes, alternating the starting position between facing an open arm and facing a closed arm. The session was recorded and an observer blind to treatment recorded the number of explorations, entries and time spent in the open arm. Explorations were defined as the rat placing two feet into an open arm without fully entering said arm. Entries were defined as the rat placing all four feet in an open arm. Time of entry in the open arm was recorded from the time the rat placed four feet in the open arm until two of the rats' feet entered the open square.

Figure 19:
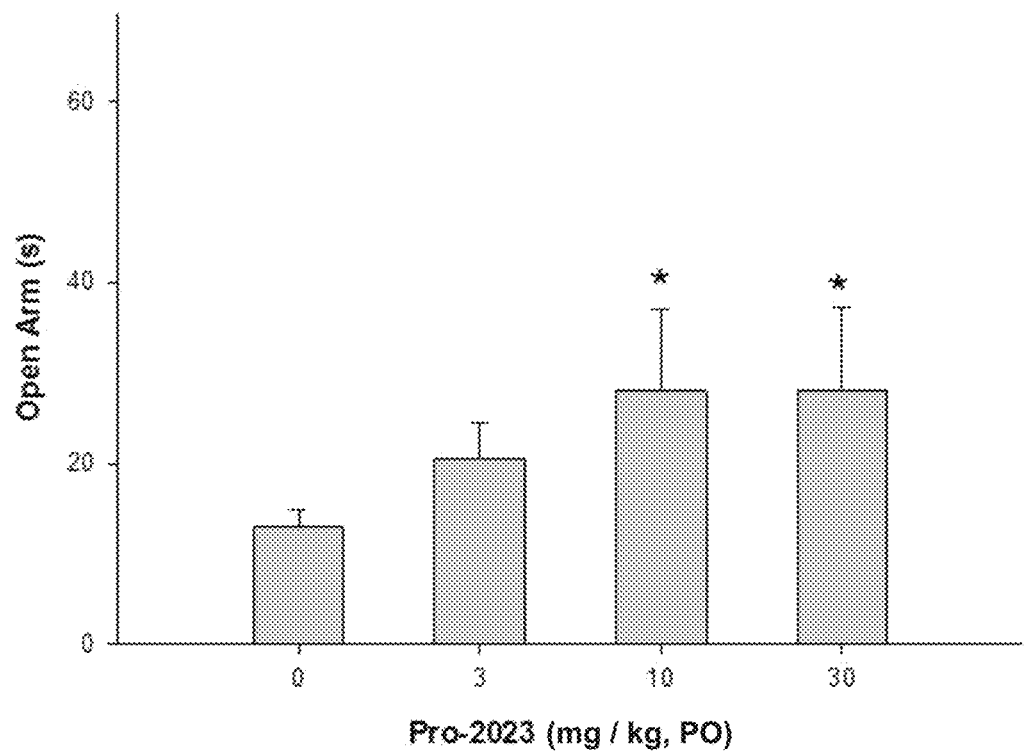
FIG. 19 is a graphical representation the total time Pro-2023 treated rats spent on the open arms of the elevated-plus maze.
Figure 20:
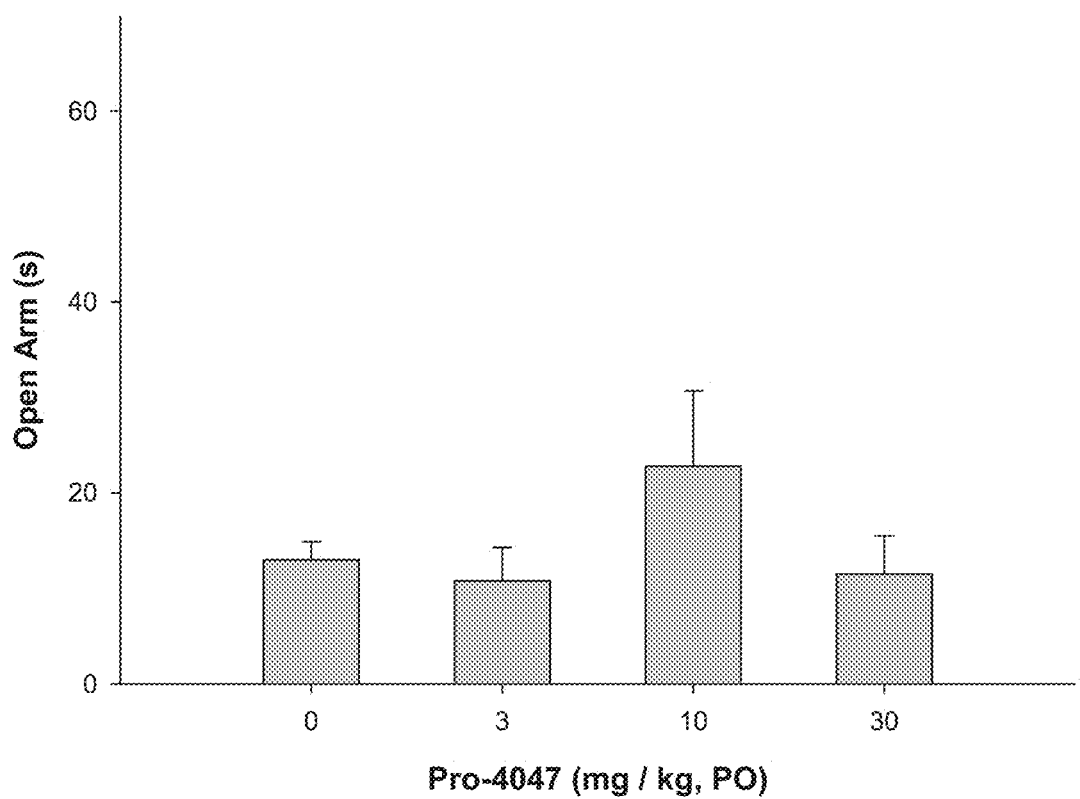
FIG. 20 is a graphical representation the total time Pro-4047 treated rats spent on the open arms of the elevated-plus maze.
Figure 21:
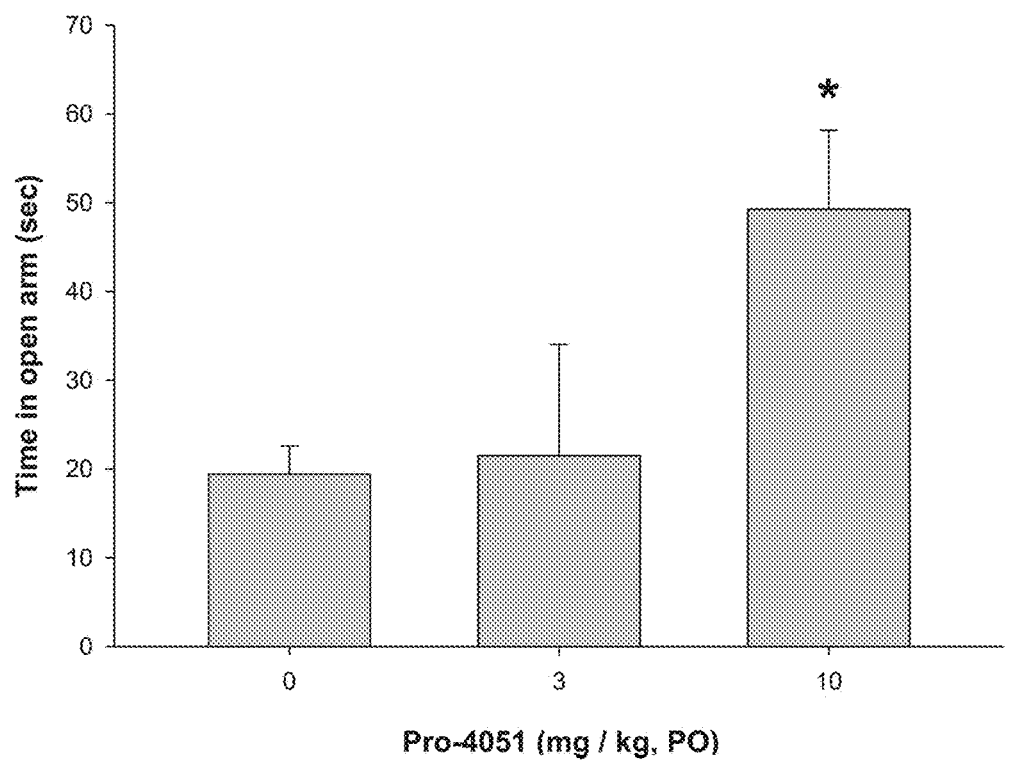
FIG. 21 is a graphical representation the total time Pro-4051 treated rats spent on the open arms of the elevated-plus maze.
Figure 22:
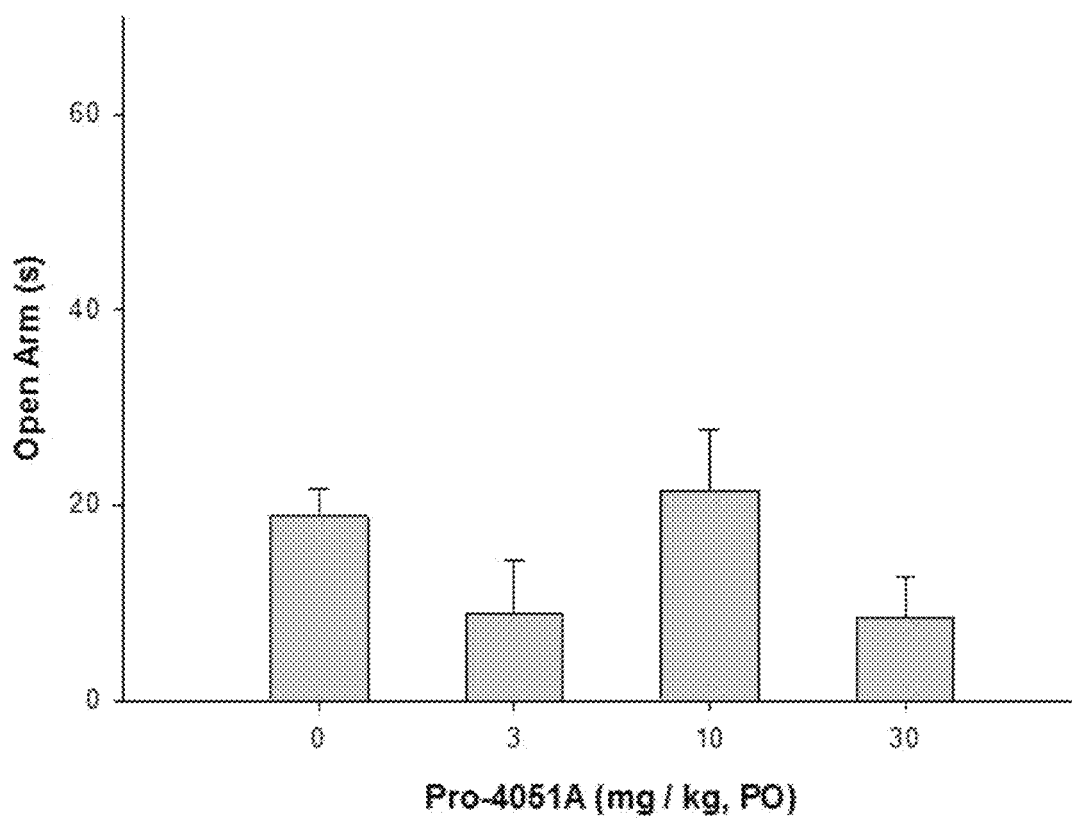
FIG. 22 is a graphical representation the total time Pro-4051a treated rats spent on the open arms of the elevated-plus maze.

After administration of a compound of the present invention, the rat increased the amount of time spend on the open arms of the maze, demonstrating a reduced anxiety and effective alleviation of symptoms associated with schizophrenia. Specifically, as seen in FIG. 19, rats treated with 10 or 30 mg/kg, PO (orally) of Pro-2023 spent around 27 seconds on the open arms. This represents an increase of time spent on the open arm of about 100%. As seen in FIG. 20, rats treated with 10 mg/kg, PO (orally) of Pro-4047 spent around 22 seconds on the open arms which is not a significant increase over control. This could be because the pharmacokinetics are such that the therapeutic window was missed with the single time-point tested. In addition, this could be due to the dose-range tested, which may be sub-threshold doses or the sample size is too small to achieve statistical significance. As seen in FIG. 21, rats treated with 10 mg/kg, PO (orally) of Pro-4051 spent around 48 seconds on the open arms or about a 150% increase over control. As seen in FIG. 22, rats treated with 10 mg/kg, PO (orally) of Pro-4051a spent around 22 seconds on the open arms which is not a significant increase over control. Thus, Pro-2023, and Pro-4051 demonstrate the ability to alleviate symptoms associated with schizophrenia in vivo.

Brain Levels of NAC and Glutathione Following Oral Administration

The goal of this experiment was to demonstrate the pharmacokinetic properties of test compounds in the brain of C57BL/6 mice.

The experiment was conducted as follows.

A compound of the invention was administered orally to C57BL/6 mice at either 10 or 100 mg/kg. Brain samples were collected at 0.25, 0.50, 1, 2 and 4 hours following the oral administration. Levels of NAC and glutathione were quantified in the brain samples using liquid chromatography-mass spectrometry (LC-MS/MS).

Figure 23:
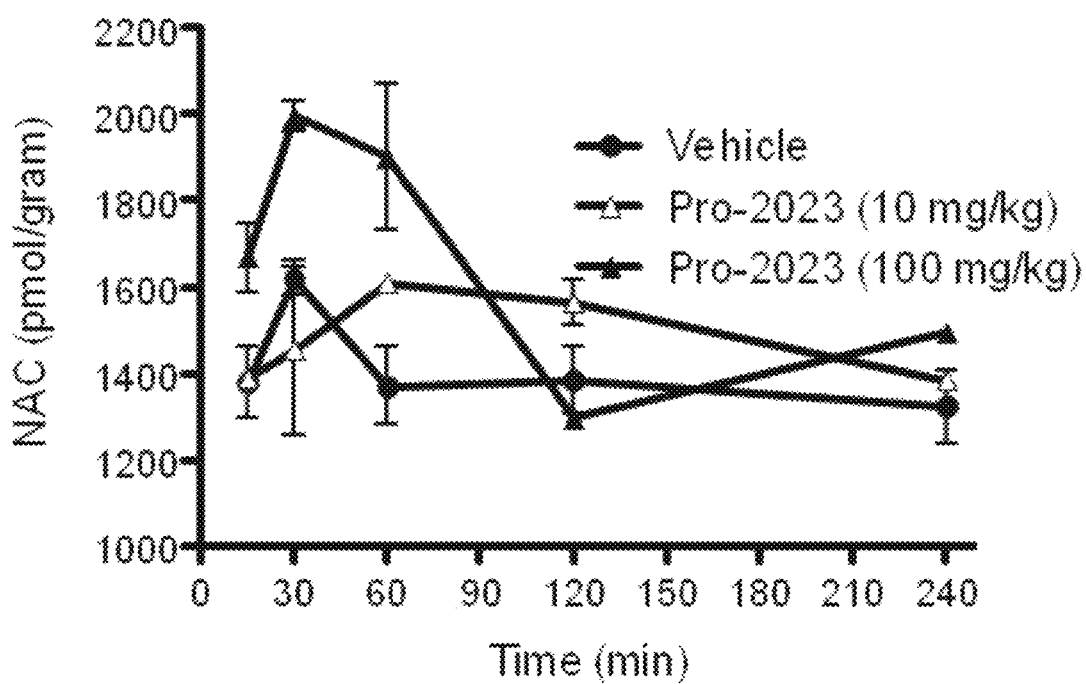
FIG. 23 is a graphical representation of levels of NAC present in the brain after oral administration of Pro-2023.

FIG. 23 depicts the levels of NAC found in the brain following oral administration of Pro-2023. At 0.5 hours oral administration of 100 mg/kg of Pro-2023 caused NAC to occur in the brain at about 2,000 pmol/g of brain tissue or about 1.25 times that of the vehicle (about 1,600 pmol/g). Surprisingly, at 1 hour NAC remained in the brain at about 1,900 pmol/g whereas the control fell back to about 1,400 pmol/g. This result represents a 1.35 times difference between NAC and the control.

Figure 24:
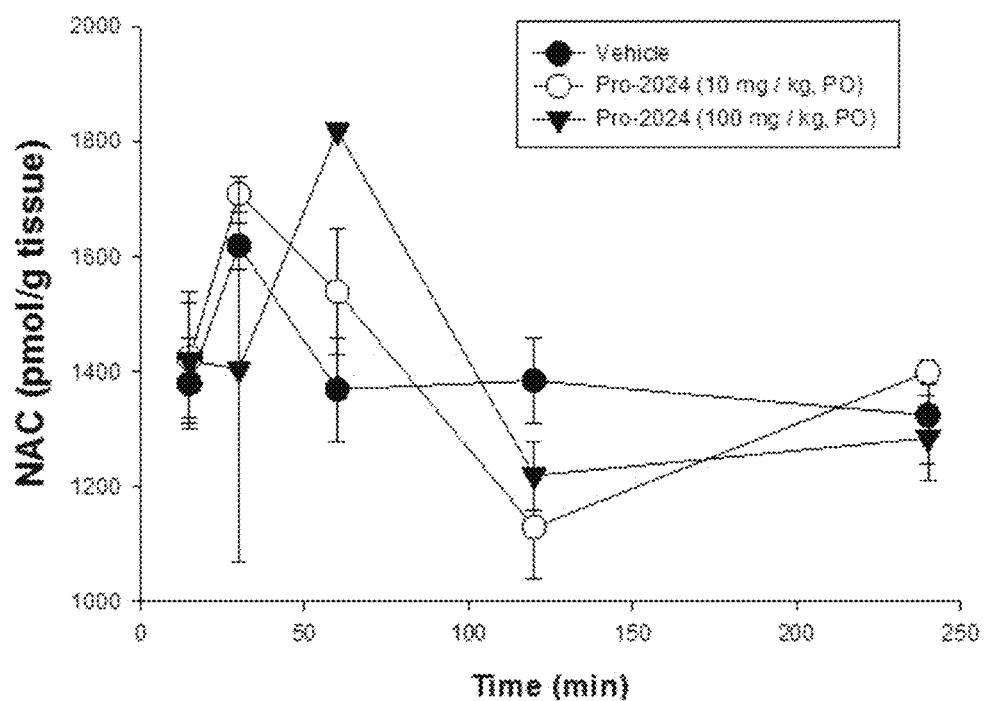
FIG. 24 is a graphical representation of levels of NAC present in the brain after oral administration of Pro-2024.

FIG. 24 depicts the levels of NAC found in the brain following oral administration of Pro-2024. At 1.0 hours oral administration of 100 mg/kg of Pro-2024 caused NAC to occur in the brain at about 1,800 pmol/g of brain tissue or about 1.29 times that of the vehicle (about 1,400 pmol/g).

Figure 25:
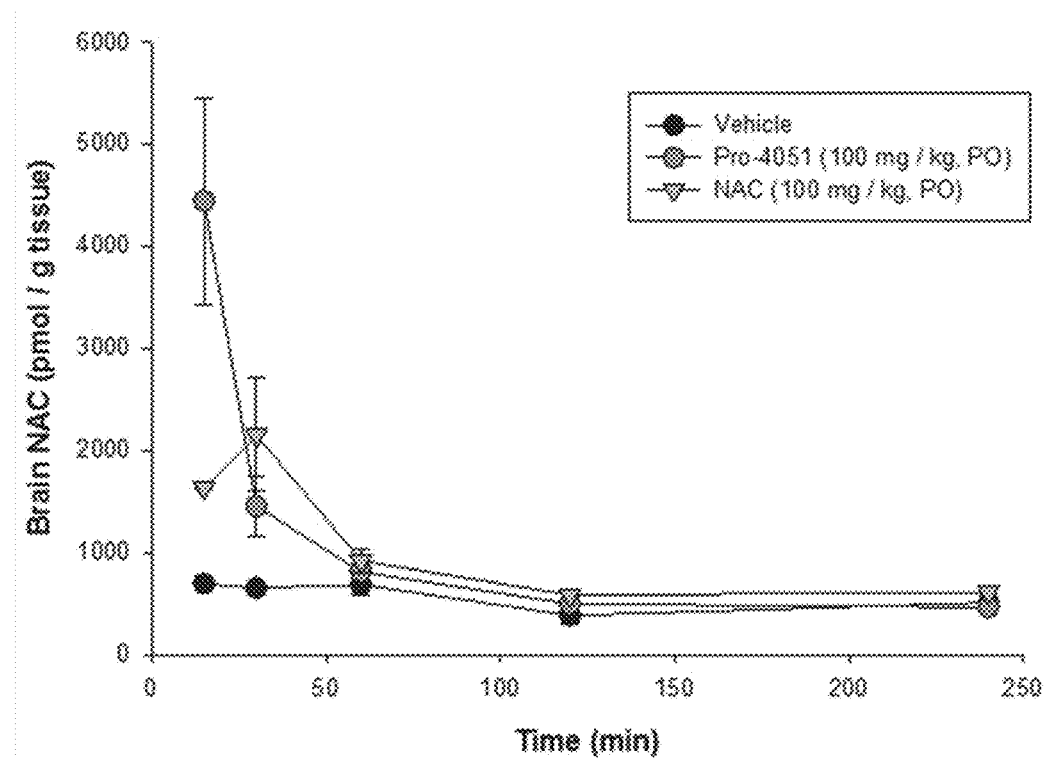
FIG. 25 is a graphical representation of levels of NAC present in the brain after oral administration of Pro-4051.

FIG. 25 depicts the levels of NAC found in the brain following oral administration of Pro-4051. At 0.25 hours oral administration of Pro-4051 caused NAC to occur in the brain at about 4,500 pmol/g of brain tissue or about 6 times that of the vehicle (about 750 pmol/g). Surprisingly, at the same time point, oral administration of Pro-4051 caused NAC to occur in the brain about 3 times more than the oral administration of NAC itself (about 1,500 pmol/g).

Figure 26:
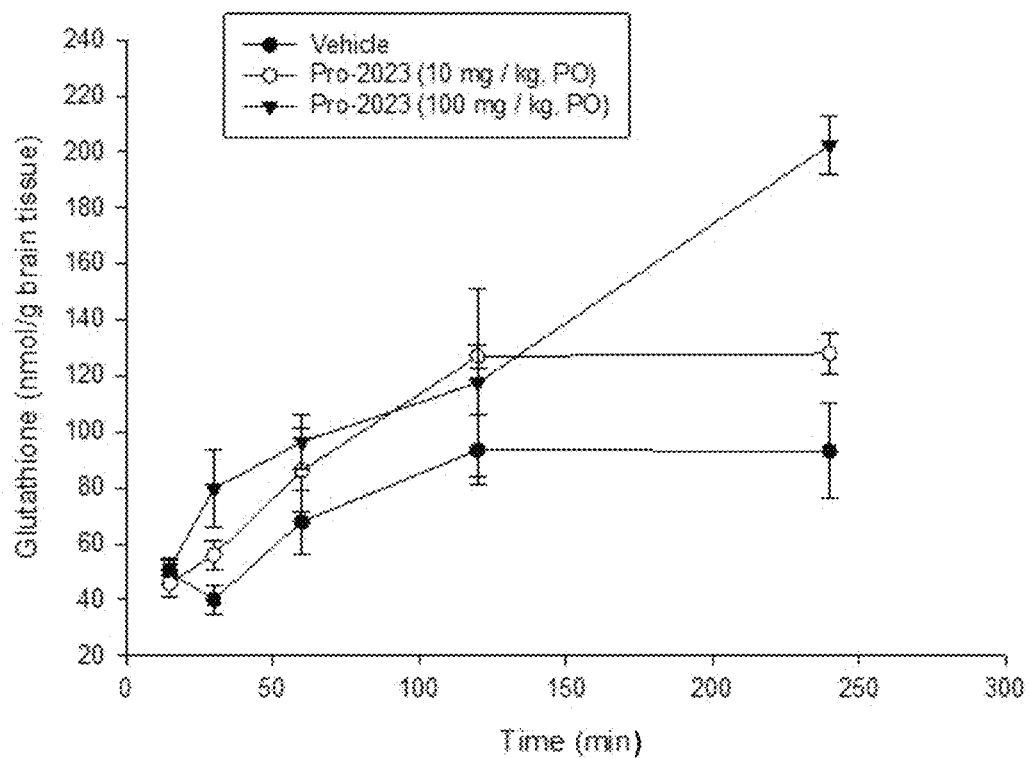
FIG. 26 is a graphical representation of levels of glutathione present in the brain after oral administration of Pro-2023.

FIG. 26 depicts the levels of glutathione found in the brain following oral administration of Pro-2023. NAC is known to elevate intracellular levels of glutathione. At 4 hours oral administration of 100 mg/kg of Pro-2023 caused glutathione to occur in the brain at about 200 nmol/g of brain tissue or about 2 times that of the vehicle (about 95 nmol/g).

Figure 27:
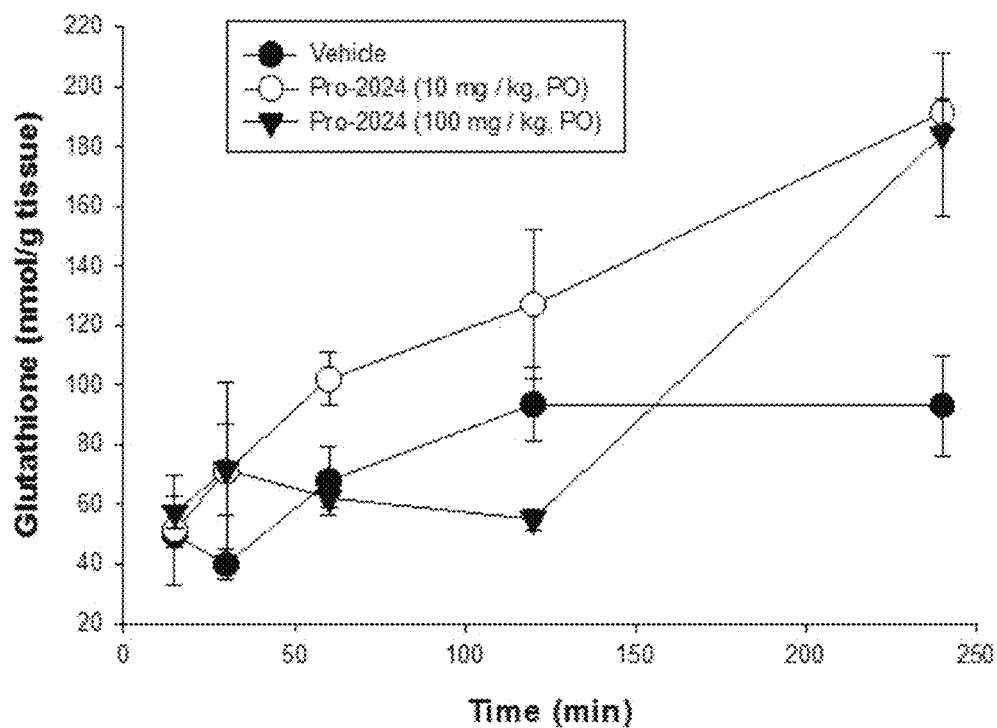
FIG. 27 is a graphical representation of levels of glutathione present in the brain after oral administration of Pro-2024.

FIG. 27 depicts the levels of glutathione found in the brain following oral administration of Pro-2024. At 4.0 hours oral administration of 10 mg/kg of Pro-2024 caused glutathione to occur in the brain at about 190 nmol/g of brain tissue or about at 2 times that of the vehicle (about 95 nmol/g).

Figure 28:
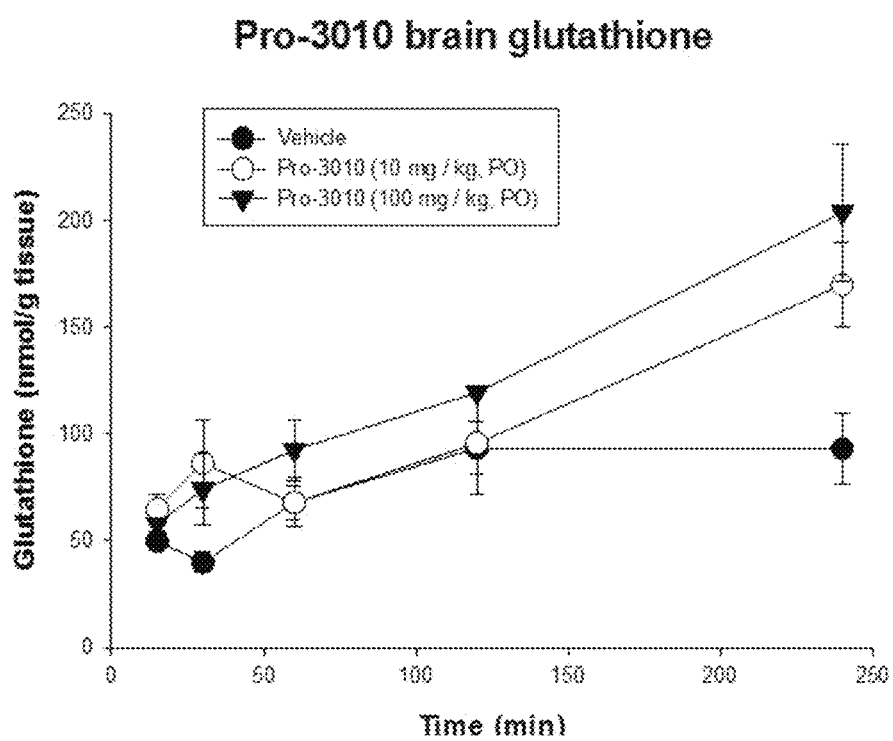
FIG. 28 is a graphical representation of levels of glutathione present in the brain after oral administration of Pro-3010.

FIG. 28 depicts the levels of glutathione found in the brain following oral administration of Pro-3010. At 4.0 hours oral administration of 100 mg/kg of Pro-3010 caused glutathione to occur in the brain at about 195 nmol/g of brain tissue or about at 2 times that of the vehicle (about 95 nmol/g).

Figure 29:
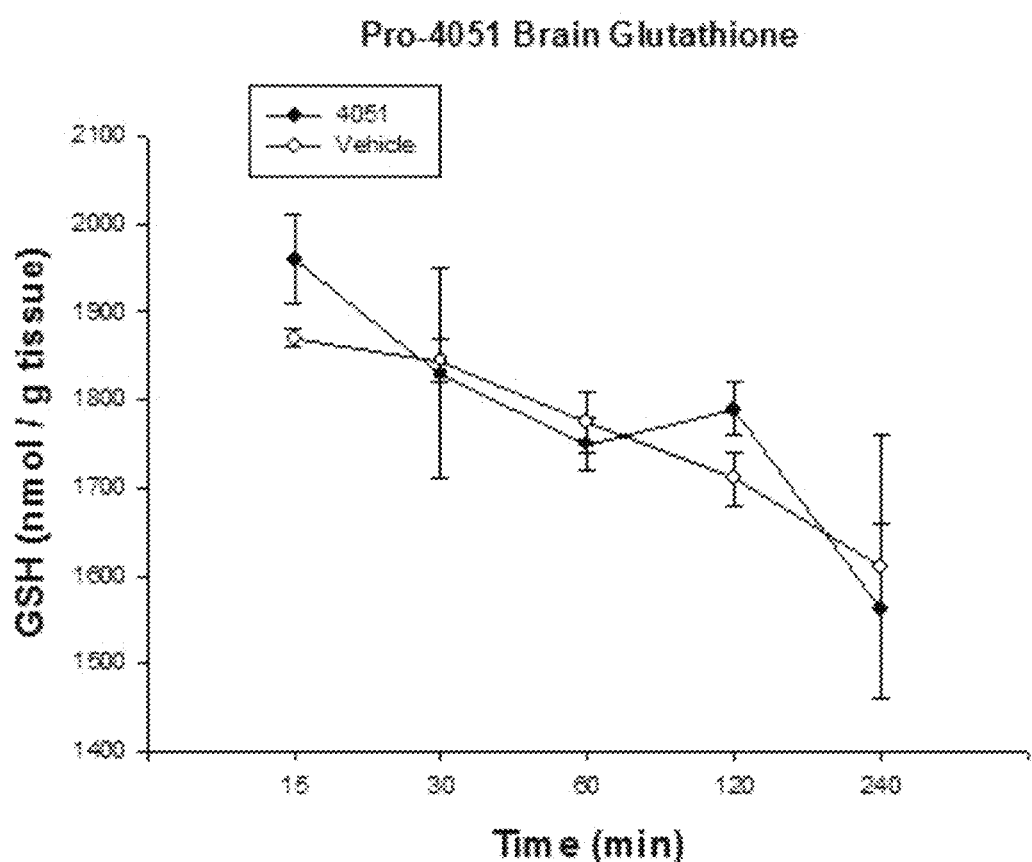
FIG. 29 is a graphical representation of levels of glutathione present in the brain after oral administration of Pro-4051.

FIG. 29 depicts the levels of glutathione found in the brain following oral administration of Pro-4051. At 4.0 hours oral administration of 100 mg/kg of Pro-4051 caused glutathione to occur in the brain at about 1960 nmol/g of brain tissue or about 1.05 times that of the vehicle (about 1870 nmol/g).

These results demonstrate that oral administration of Pro-2023 or Pro-4051 and possibly Pro-2024 are able to more effectively elevate levels of NAC in the brain than the oral administration of NAC itself and thus may be more effective than NAC for the treatment of CNS diseases, such as schizophrenia, that currently respond to large doses of NAC. In addition, these compounds, along with Pro-3010, have demonstrated the ability to increase glutathione in the brain.

What is claimed is:

1. A method of treating trichotillomania comprising administering a therapeutically effective amount of the compound of formula I

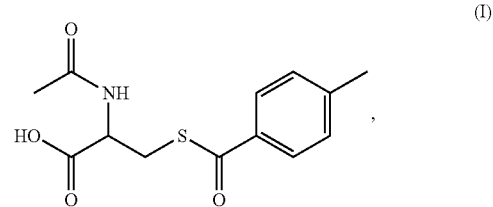 [SMILES: CC(=O)NC(CSC(=O)c1ccc(C)cc1)C(=O)O]

(I)

to a human in need thereof.

2. The method of claim 1, wherein the compound of formula I is administered orally.

3. The method of claim 1, wherein the compound of formula I is administered rectally, parenterally, intracisternally, intravaginally, transdermally, transmucosally, sublingually, pulmonarily, intraperitoneally, topically, or bucally.

4. The method of claim 1, wherein the compound of formula I is administered in a solid form.

5. The method of claim 1, wherein the compound of formula I is administered in a capsule.

6. The method of claim 1, wherein the compound of formula I is administered in a soft gelatin capsule.

7. The method of claim 1, wherein the compound of formula I is administered in a hard gelatin capsule.

8. The method of claim 1, wherein the compound of formula I is administered as a tablet.

9. The method of claim 1, wherein the compound of formula I is administered in a solid form with an enteric coating.

10. The method of claim 1, wherein the compound of formula I is administered in a composition that releases the compound in a delayed manner.

11. The method of claim 1, wherein the compound of formula I is administered in a composition that releases the compound in the intestinal tract.

12. The method of claim 1, wherein the compound of formula I is administered in a liquid form.

13. The method of claim 1, wherein from about 0.0001 to about 2,000 mg/kg of the compound of formula I is administered to the subject in one day.

14. The method of claim 1, wherein from about 0.001 to about 15 mg/kg of the compound of formula I is administered to the subject in one day.

15. The method of claim 1, wherein the compound of formula I is administered in a pharmaceutical composition containing a pharmaceutically acceptable carrier.

16. The method of claim 1, wherein the therapeutically effective amount of the compound of formula I is administered in multiple doses in a day.

17. The method of claim 1, wherein the therapeutically effective amount of the compound of formula I is administered in a single dose in a day.

18. The method of claim 1, wherein the compound of formula I is the compound

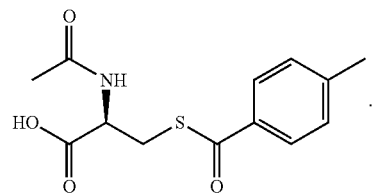 [SMILES: CC(=O)N[C@@H](CSC(=O)c1ccc(C)cc1)C(=O)O]

19. A method of treating trichotillomania comprising administering a therapeutically effective amount of a salt or ester of the compound of formula I

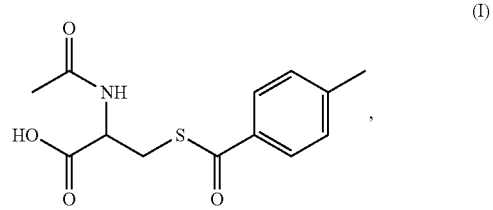 [SMILES: CC(=O)NC(CSC(=O)c1ccc(C)cc1)C(=O)O]

to a human in need thereof.

20. The method of claim 19, wherein a salt of the compound of formula I is administered.

21. The method of claim 20, wherein the salt is an organic amine.

* * * * *